US011965150B2

(12) United States Patent
Baker, Jr. et al.

(10) Patent No.: US 11,965,150 B2
(45) Date of Patent: *Apr. 23, 2024

(54) SYSTEM AND METHOD FOR VAPORIZED HYDROGEN PEROXIDE CLEANING OF AN INCUBATION CHAMBER

(71) Applicant: Caron Products and Services, Inc., Marietta, OH (US)

(72) Inventors: Milton Ford Baker, Jr., Vincent, OH (US); Dale C. Barnett, Marietta, OH (US); Robert W. Dotterer, Sardis, OH (US); David N. Figel, Caldwell, OH (US); Stephen Charles Keiser, Vienna, WV (US)

(73) Assignee: CARON PRODUCTS AND SERVICES, INC., Marietta, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,199

(22) Filed: Oct. 10, 2022

(65) Prior Publication Data
US 2023/0148051 A1 May 11, 2023

Related U.S. Application Data

(63) Continuation of application No. 16/877,826, filed on May 19, 2020, now Pat. No. 11,525,114, which is a
(Continued)

(51) Int. Cl.
*C12M 1/12* (2006.01)
*A61L 2/20* (2006.01)
(Continued)

(52) U.S. Cl.
CPC ............ *C12M 37/00* (2013.01); *A61L 2/208* (2013.01); *C12M 37/06* (2013.01); *C12M 41/14* (2013.01); *C12M 41/48* (2013.01); *A61L 2202/14* (2013.01)

(58) Field of Classification Search
CPC ... A61L 2/04; A61L 2/10; A61L 2/208; A61L 2202/122; A61L 2202/13; A61L 2202/14;
(Continued)

(56) References Cited

U.S. PATENT DOCUMENTS

| 4,863,688 A | 9/1989 | Schmidt et al. |
| 5,328,597 A | 7/1994 | Boldt, Jr. et al. |

(Continued)

FOREIGN PATENT DOCUMENTS

EP    0984274 A2    8/1999

OTHER PUBLICATIONS

Sanyo Handbook—Incubation; CO2 Incubators, Model MCO-10AIC(UV); MCO-19AIC ; p. 1-6.
(Continued)

*Primary Examiner* — Douglas Lee
(74) *Attorney, Agent, or Firm* — John L. DeAngelis; Wolter, Van Dyke, Davis, PLLC

(57) ABSTRACT

A method is provided for vaporized hydrogen peroxide cleaning of a chamber. The method includes altering a temperature of air in the chamber from an initial temperature to a sterilization temperature over a first time period. The method also includes injecting vaporized hydrogen peroxide into air in the chamber to alter a relative humidity of hydrogen peroxide vapor in the chamber to a sterilization level over the first time period. The method also includes maintaining the temperature at the sterilization temperature and the relative humidity at the sterilization level over a second time period. The method also includes reducing the relative humidity from the sterilization level to a safe level over a third time period. In one embodiment, the method is provided for vaporized hydrogen peroxide cleaning of an
(Continued)

interior chamber of an incubation container. In other embodiments, the incubation chamber featured in the method is provided.

20 Claims, 25 Drawing Sheets

Related U.S. Application Data continuation of application No. 15/382,915, filed on Dec. 19, 2016, now Pat. No. 10,738,271.

(60) Provisional application No. 62/269,918, filed on Dec. 18, 2015.

(51) Int. Cl.
*C12M 1/00* (2006.01)
*C12M 1/36* (2006.01)

(58) Field of Classification Search
CPC ... A61L 2202/24; C12M 37/00; C12M 37/06; C12M 41/14; C12M 41/48
See application file for complete search history.

(56) References Cited

U.S. PATENT DOCUMENTS

| | | | |
|---|---|---|---|
| 6,228,324 B1 | 5/2001 | Hasegawa et al. | |
| 6,506,605 B1 | 1/2003 | Allen et al. | |
| 7,700,056 B2 | 4/2010 | Hill et al. | |
| 7,981,361 B2 | 7/2011 | Bacik | |
| 10,738,271 B2 * | 8/2020 | Baker, Jr. | A61L 2/208 |
| 11,525,114 B2 * | 12/2022 | Baker, Jr. | A61L 2/208 |
| 2002/0146817 A1 | 10/2002 | Cannon et al. | |
| 2006/0008378 A1 | 1/2006 | Imai et al. | |
| 2007/0274858 A1 | 11/2007 | Childrers et al. | |
| 2009/0041617 A1 | 2/2009 | Lee | |
| 2009/0060781 A1 | 3/2009 | Adams | |
| 2011/0076189 A1 | 3/2011 | McVey et al. | |
| 2011/0076192 A1 | 3/2011 | Robitaille et al. | |
| 2011/0315783 A1 | 12/2011 | Baker et al. | |
| 2012/0219456 A1 * | 8/2012 | Childers | A61L 2/208 422/547 |
| 2013/0089461 A1 | 4/2013 | Hanada | |
| 2014/0056765 A1 | 2/2014 | Henriot | |
| 2014/0105785 A1 | 4/2014 | Hill | |
| 2014/0205499 A1 | 7/2014 | Sakaki | |
| 2017/0175069 A1 | 6/2017 | Baker, Jr. et al. | |
| 2020/0360552 A1 | 11/2020 | Baker, Jr. et al. | |

OTHER PUBLICATIONS

Steris Corp.—Vaporized Hydrogen Peroxide (VHP) Advanced Biodecontamination Solutions (ABS): Green Technology for the Highest Level of Microbial Control within a Life Science Facility; p. 1-52.

Steris Corp.—Eradicate the Invisible Threat with Vaporizied Hydrogen Peroxide (VHP) and the Biodecontamination Service Professionals at B & V; p. 1-17.

Lin, ESCO Technologies—Worldwide—Decontamination of ESCO Class II Biosafety Cabinet using Vaporized Hydrogen Peroxide. p. 1-6.

Sanyo Handbook—Cell Culture CO2 Incubator, Model MCO-19AIC. p. 1-7.

\* cited by examiner

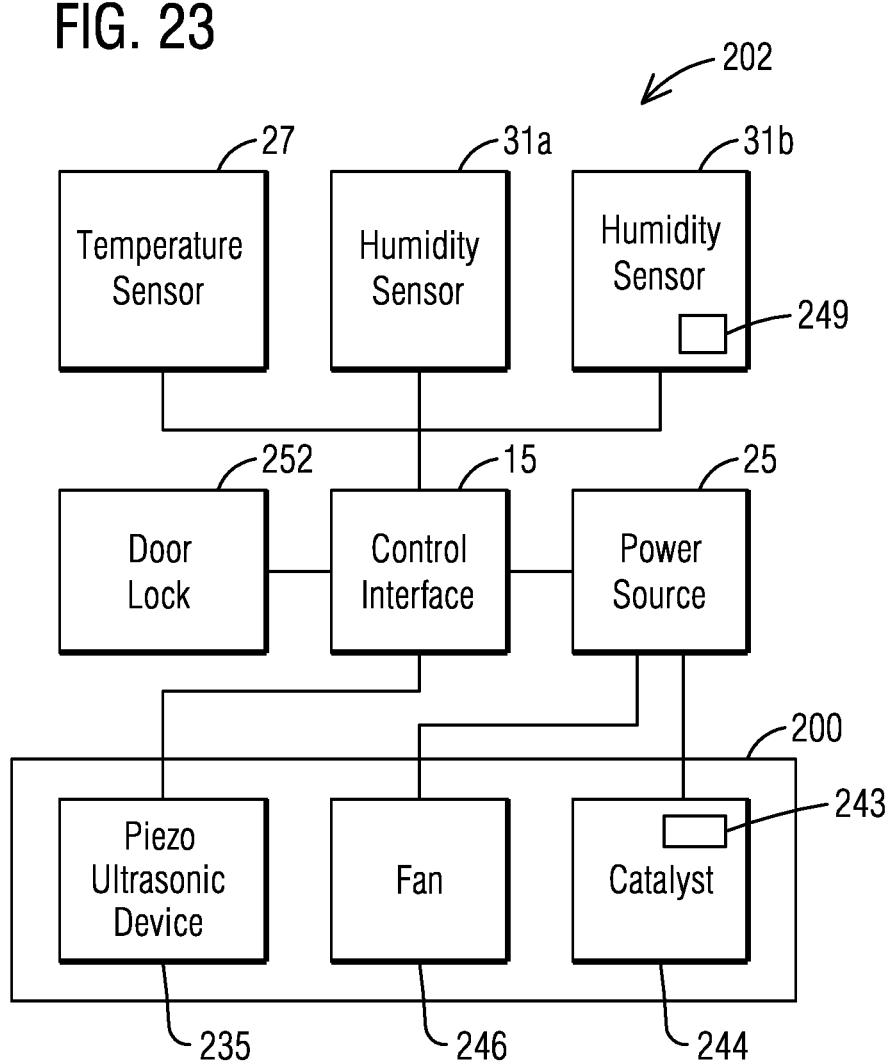

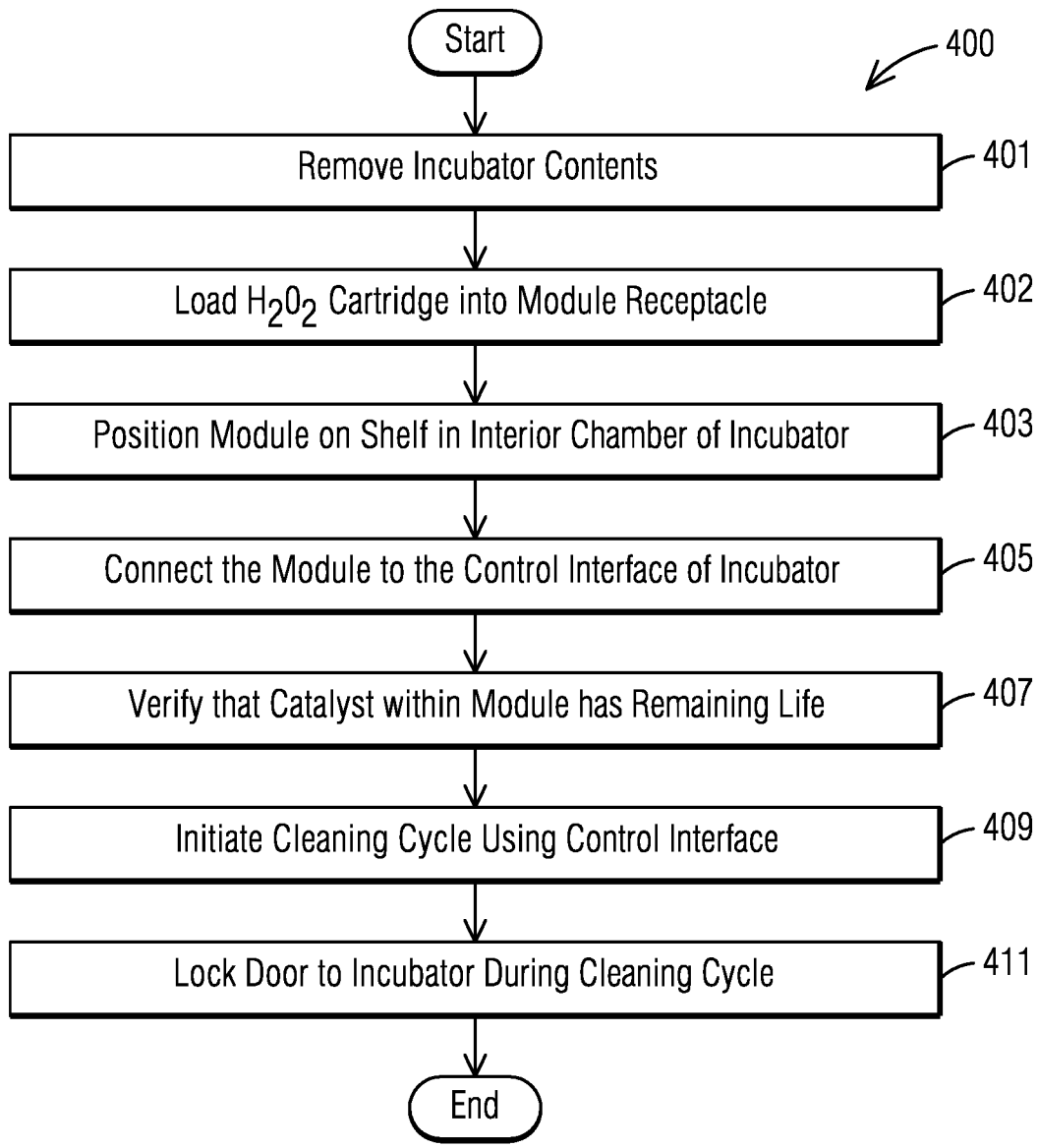

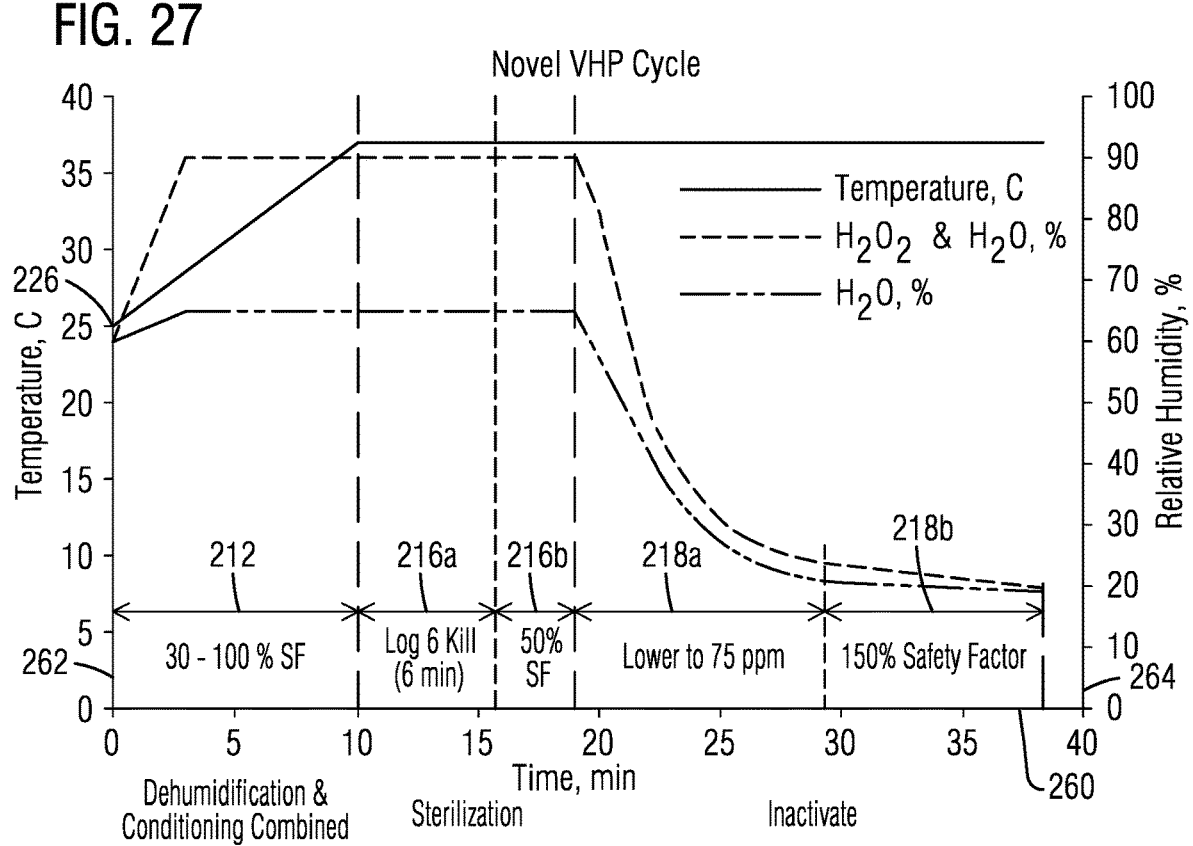
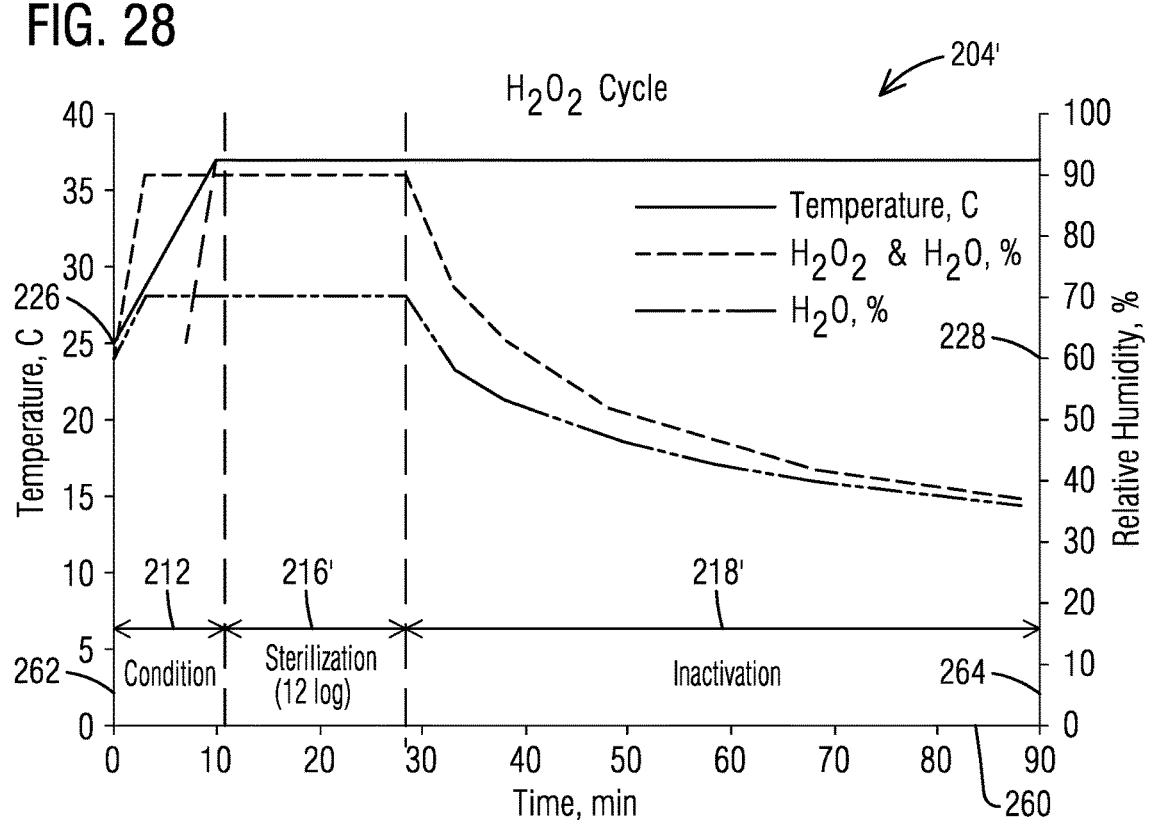

SYSTEM AND METHOD FOR VAPORIZED HYDROGEN PEROXIDE CLEANING OF AN INCUBATION CHAMBER

CROSS-REFERENCE TO RELATED APPLICATIONS

This application claims priority to, as a continuation application, the non-provisional application filed May 19, 2020, assigned application Ser. No. 16/877,826, titled "System and Method for Vaporized Hydrogen Peroxide Cleaning of An Incubation Chamber" and further claims priority to assigned application Ser. No. 15/382,915, titled "System and Method for Vaporized Hydrogen Peroxide Cleaning of An Incubation Chamber" filed Dec. 19, 2016 and further claims priority to the provisional application filed on Dec. 18, 2015 and the entire contents of which are hereby incorporated by reference as if fully set forth herein, under 35 U.S.C. § 119(e).

BACKGROUND OF THE INVENTION

Mammalian cell culturing in an incubation chamber is typically conducted at simulated human body conditions of 37 C (98.6 F) and moist environments (humidity 90%, just below dew point where condensation occurs). While mammalian cells grow best at these conditions, so does bacterial cells, mold and other unwanted organisms. These menaces can contaminate and ruin cell culture studies. For this reason, periodic decontamination and/or sterilization cycles are performed on cell culture equipment.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

FIG. 23 is a partial block diagram of the embodiment of the system of FIG. 19.

FIG. 24 is a flowchart depicting one embodiment of a method for operating the system of FIG. 19 during a vaporized hydrogen peroxide cleaning of the incubation chamber.

FIG. 27 is a graph that shows one embodiment of temperature and humidity levels during a H202 cleaning cycle using the system of FIG. 19.

FIG. 28 is a graph that shows one embodiment of temperature and humidity levels during a H202 cleaning cycle using the system of FIG. 19.

Similar numbers refer to similar parts throughout the drawings.

DETAILED DESCRIPTION OF THE INVENTION

There are several well-established and effective methods of contamination control in an incubation chamber for use in cell culturing. They include:

Manually wiping the chamber with a cleaning agent such as H2O2
Introducing moist air at 90 C into the chamber
Introducing dry air at 140 C into the chamber Introducing dry air at 180 C into the chamber Employing a HEPA (high efficiency particulate air) filter Introducing UV (ultraviolet) germicidal light into the chamber Introducing chloride dioxide gas into the chamber Using formalin/paraformaldehyde Introducing vaporized hydrogen peroxide (H2O2) (wet) into the chamber Introducing vaporized hydrogen peroxide (H2O2) (dry) into the chamber The use of H2O2 vaporized hydrogen peroxide is one of the fastest methods (taking minutes instead of hours) and the market is gravitating in that direction.

One prior art H2O2 cleaning cycle utilizes a 'wet' H2O2 cycle that is cumbersome to use, expensive, labor intensive, and simply not practical. As a result, this cleaning cycle has not been well received by users.

A conventional H2O2 cycle comprises four basic steps. This list of steps below does not include the preparatory and post-cleaning work in setting up the equipment and then removing it when cleaning is complete.

1. Dehumidify the chamber air to increase its moisture-absorption capacity by:
    A. Dehumidifying using mechanical refrigeration (like a household dehumidifier); or
    B. Raising the temperature of the chamber air since the capacity of air to retain moisture increases as the temperature increases.
2. Condition the air with H2O2 according to:
    A. A dry cycle conditioning technique by increasing the relative humidity to about 90% and injecting H2O2 during this process. This 90% value represents about the maximum amount of moisture the air can hold without risking condensation; or
    B. A wet cycle conditioning cycle technique by fogging the air with H2O2 solution until its saturation point is reached. Condensation will occur when using this approach.

Generally, during a dry cycle, as the name implies, there is no condensation within the chamber. If the user touches the interior walls they will feel 'dry'. Condensation occurs during a wet cycle and the chamber interior surfaces become damp with H2O2. At the end of a 'wet' cycle, H2O2 (or H2O once the H2O2 has been decomposed) will be pooled up on the chamber floor in a puddle.

3. Sterilize the chamber by holding the H2O2 conditions for a specified time needed to 'kill' the unwanted cells, i.e., about three to fifteen minutes at 37 C and longer at lower temperatures 4. Inactivate the H2O2.

Figure 18:
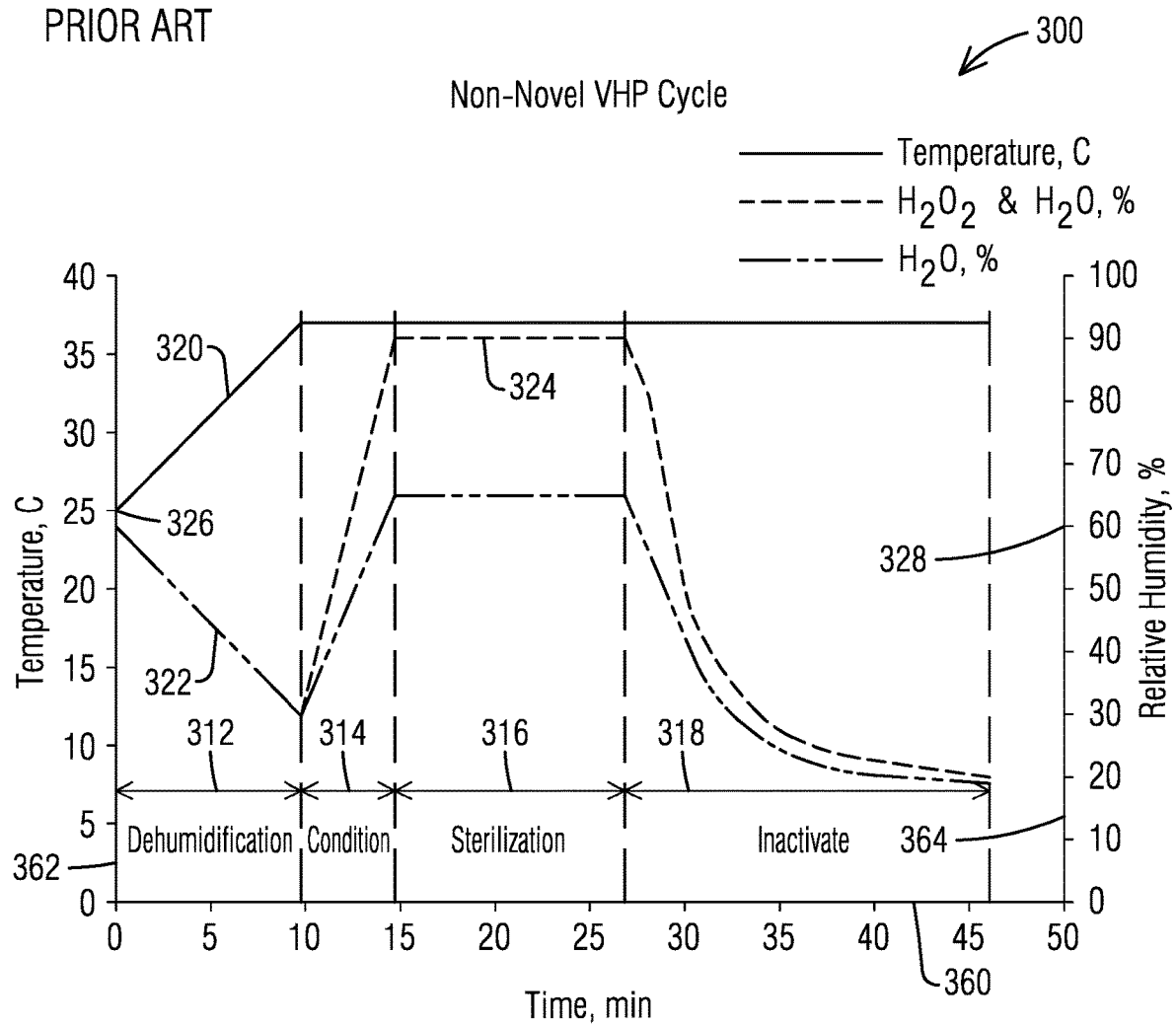
FIG. 18 is a graph that shows temperature and humidity levels during a conventional H202 cleaning cycle of an incubator.

While the H2O2 kills unwanted cells, it is also harmful to good cells. A very low level of H2O2 (as measured in ppm) must be reached (during the inactivation step) before the chamber air is safe for human exposure. Any one or a combination of several different techniques can be employed to remove/decompose the H2O2 into water (H2O) and oxygen (O2).
    A. Wait a period of time. H2O2 is naturally unstable and decomposes over time
    B. Accelerate the process by elevating the air temperature
    C. Accelerate the process by using UV light
    D. Accelerate the process by using a catalyst such as silver Another prior art decontamination cycle is described below and illustrated in a graph 300 in FIG. 18. Horizontal axis 360 is time in units of minutes. Left vertical axis 362 is temperature in units of Celsius (C). Right vertical axis 364 is relative humidity in percentage (%).

1. Dehumidify the chamber by increasing an air temperature 320 over a first time period 312 from an initial temperature 326 to an interior temperature of 37 C (Method 1B from 'basic four steps'). This causes the relative humidity 322 to drop from an initial humidity 328 (e.g. 60% rh) to 30% rh. That means the air can handle an additional amount of moisture equivalent to the amount of humidity 322 removed (additional 30%=60%-30%). The total amount of moisture that the air can absorb is now 60% (=90%-30%). 90% is the total amount of moisture that air can handle and avoid condensation. (99% is the theoretical value, but this is not practical in an incubator.) 30% relative humidity is the amount of water in the air at the end of the dehumidification phase. The difference between these two values is 60% and represents the additional amount of moisture that can be added to the air. This step takes the first time period 312, which is about ten minutes.

2. Inject H2O2 (H2O2) of some concentration (e.g. 35%) such that a combined humidity 324 of H20 and H202 reaches 90% rh. The combined humidity 324 at about 90% is a combination of H2O (water) and H2O2 (hydrogen peroxide) vapor. The humidity 322 indicates only H2O vapor at 65% (30% was already in the air plus when injecting the H2O2 additional water vapor is injected into the air). The difference between the combined humidity 324 and humidity 322 (e.g. 25%) then is the amount of H2O2 in the air. This conditioning step takes a second time period 314, which is about five minutes.

3. Hold the temperature 320 and combined humidity 324 (e.g. H2O2 levels) constant during the sterilization step over a third time period 316, which is about twelve minutes duration.

4. At the beginning of the H2O2 inactivate step turn on a fan that blows air through a silver catalyst (Method 4D from 'basic four steps'). The catalyst converts the H2O2 to harmless H2O and O2. As the combined humidity level 324 approaches the humidity 322 (at about 46 minutes of elapsed time) the amount of H2O2 approaches 0 and it is then safe for human exposure. The temperature 320 stays at 37 C as elevated temperature accelerates the reaction too. This step takes a fourth time period 318, that lasts about twenty minutes.

Figure 1:
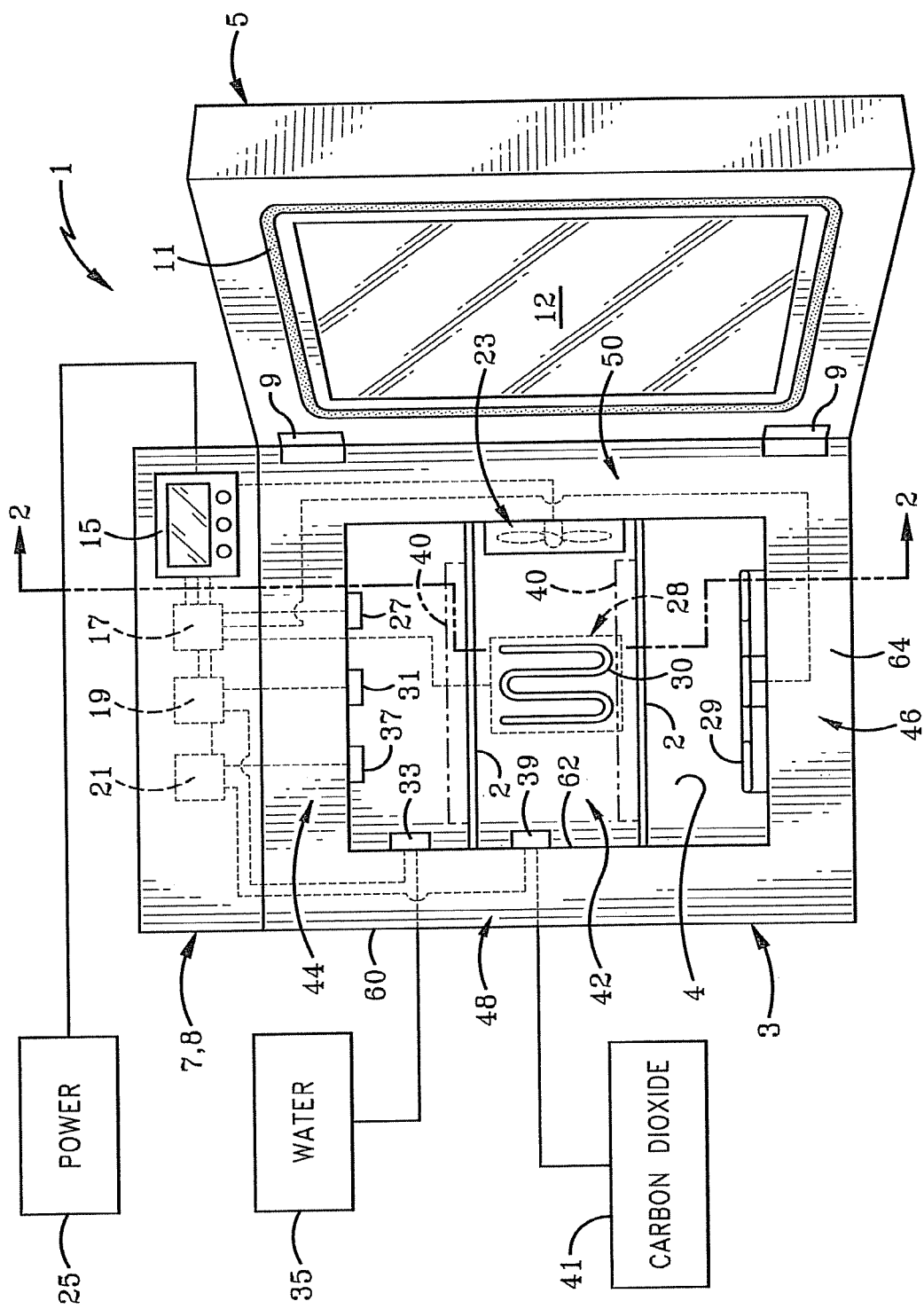
FIG. 1 is a front elevational view of a first embodiment of the insulated chamber of the present invention with portions shown diagrammatically.
Figure 4:
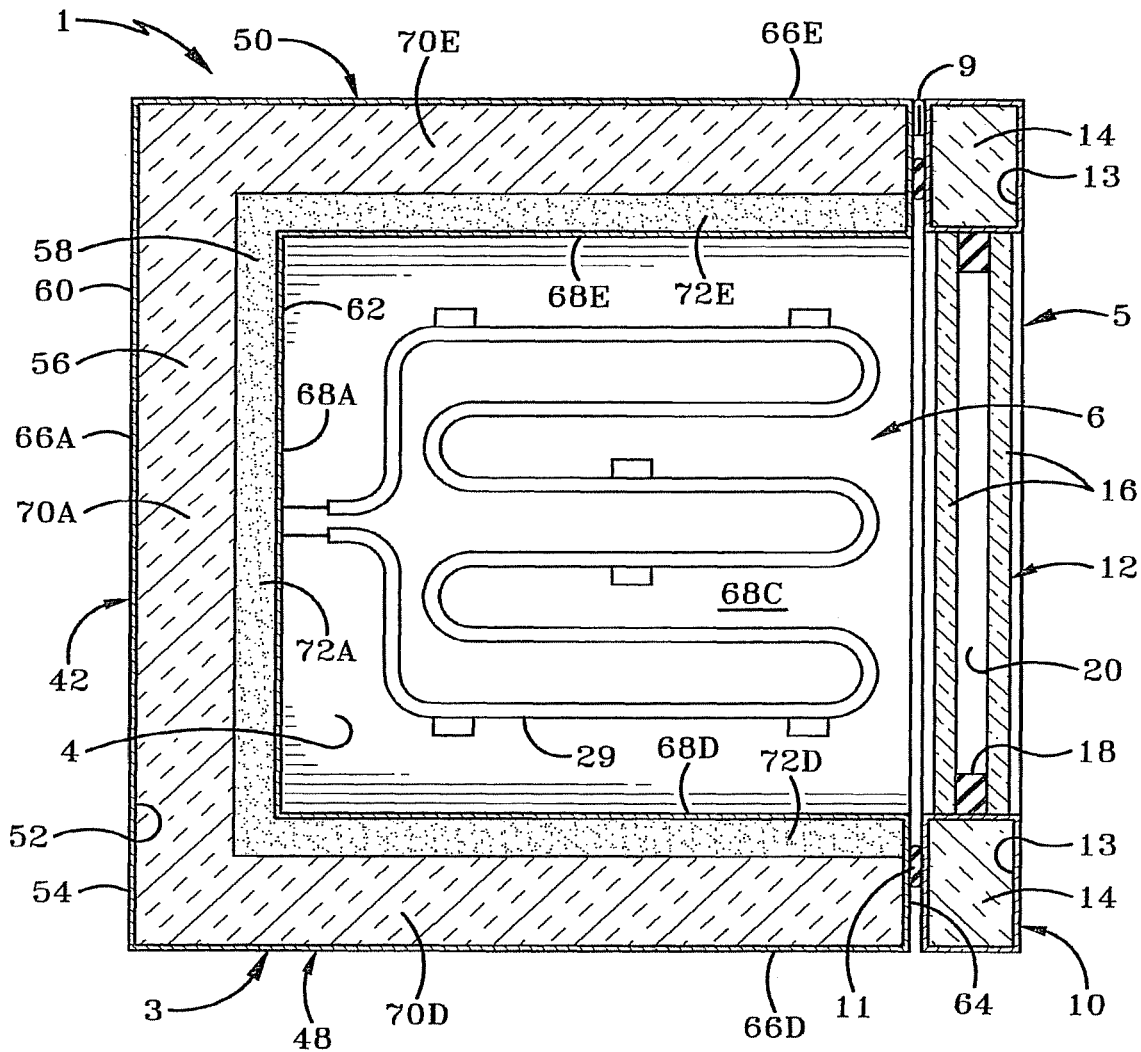
FIG. 4 is a sectional view taken on Line 4-4 of FIG. 2.
Figure 5:
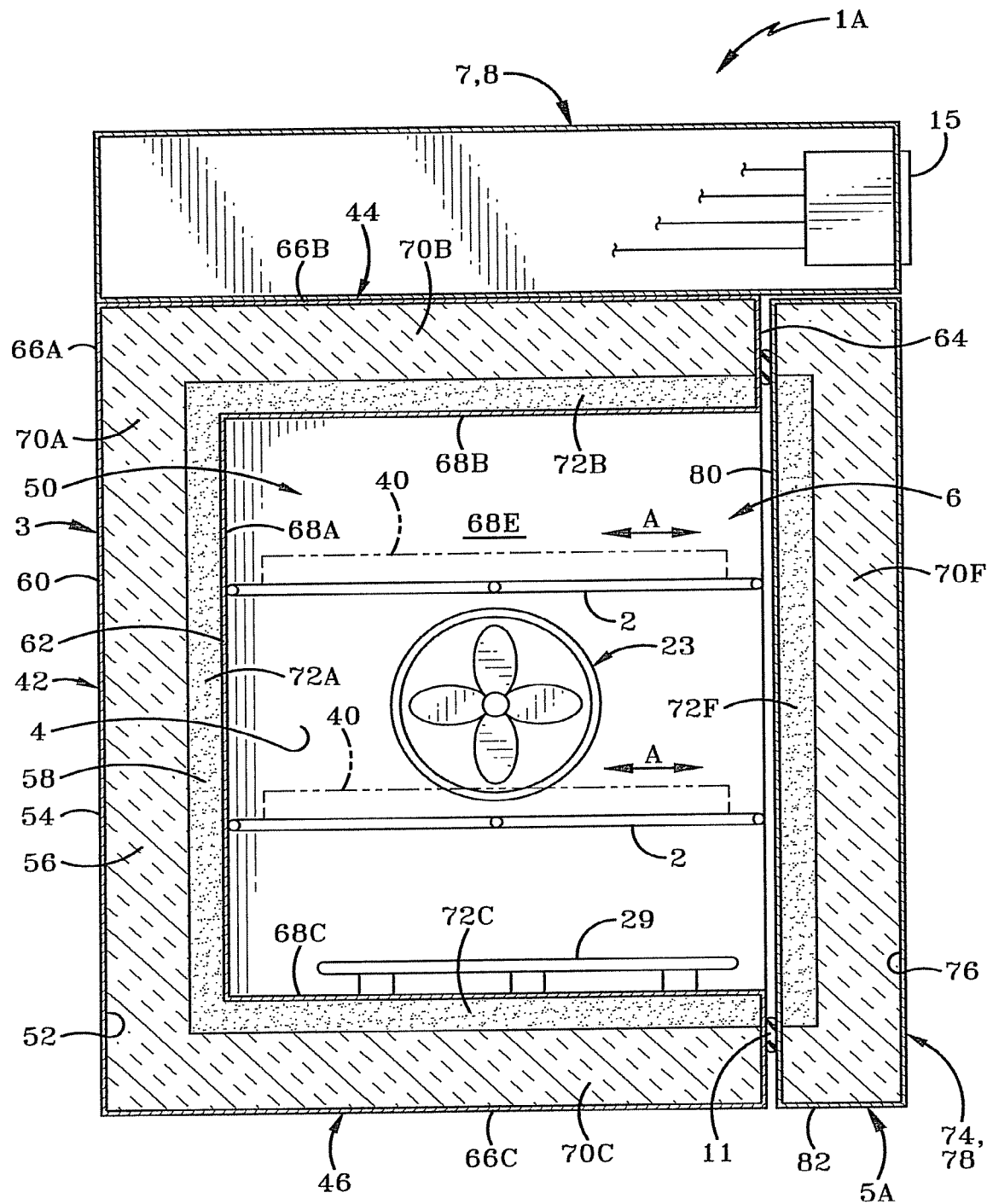
FIG. 5 is similar to FIG. 2 and is a sectional view of a second embodiment of the chamber of the present invention.
Figure 7:
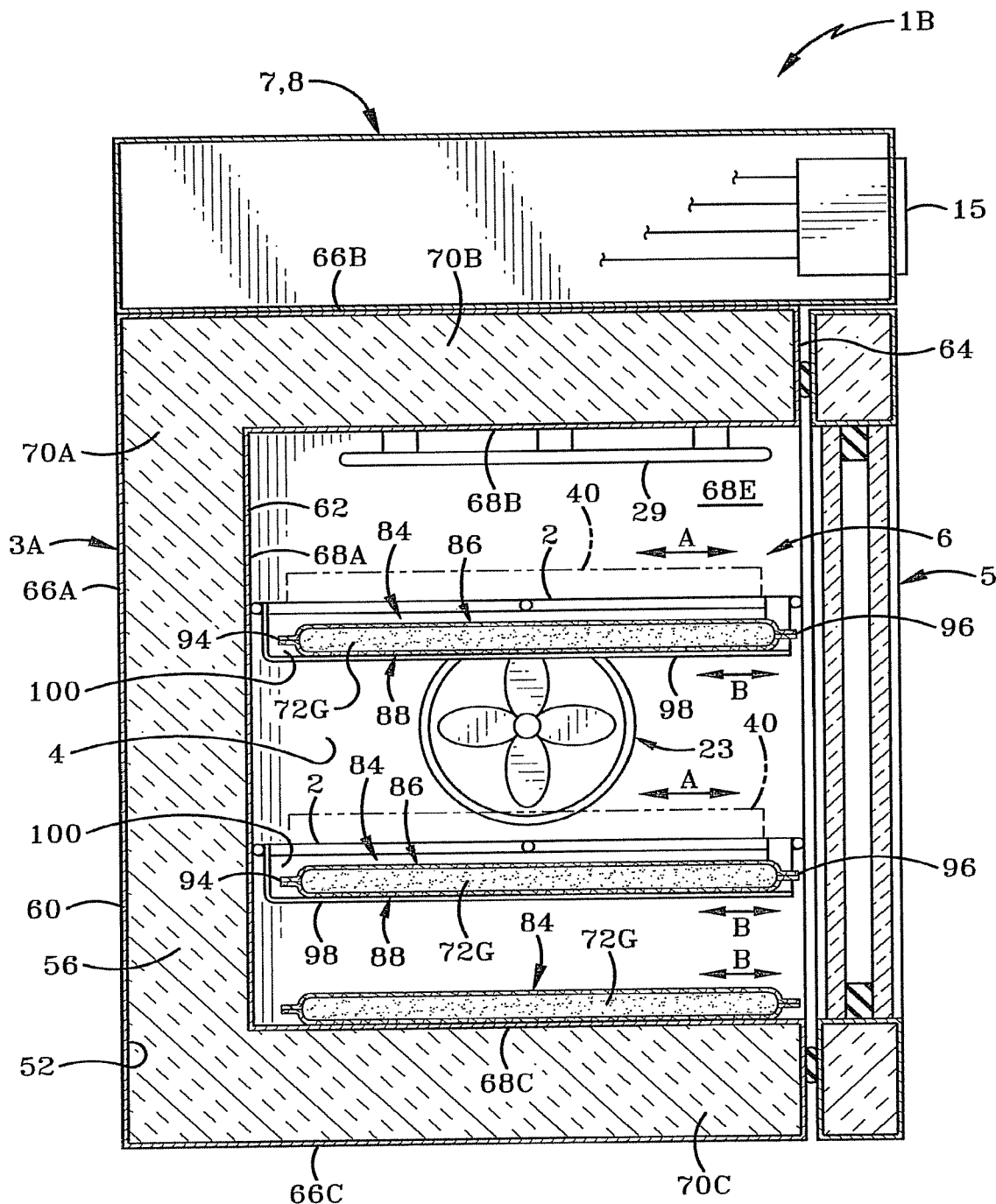
FIG. 7 is a sectional view similar to FIG. 2 of a third embodiment of the chamber of the present invention utilizing the phase change material packets.
Figure 8:
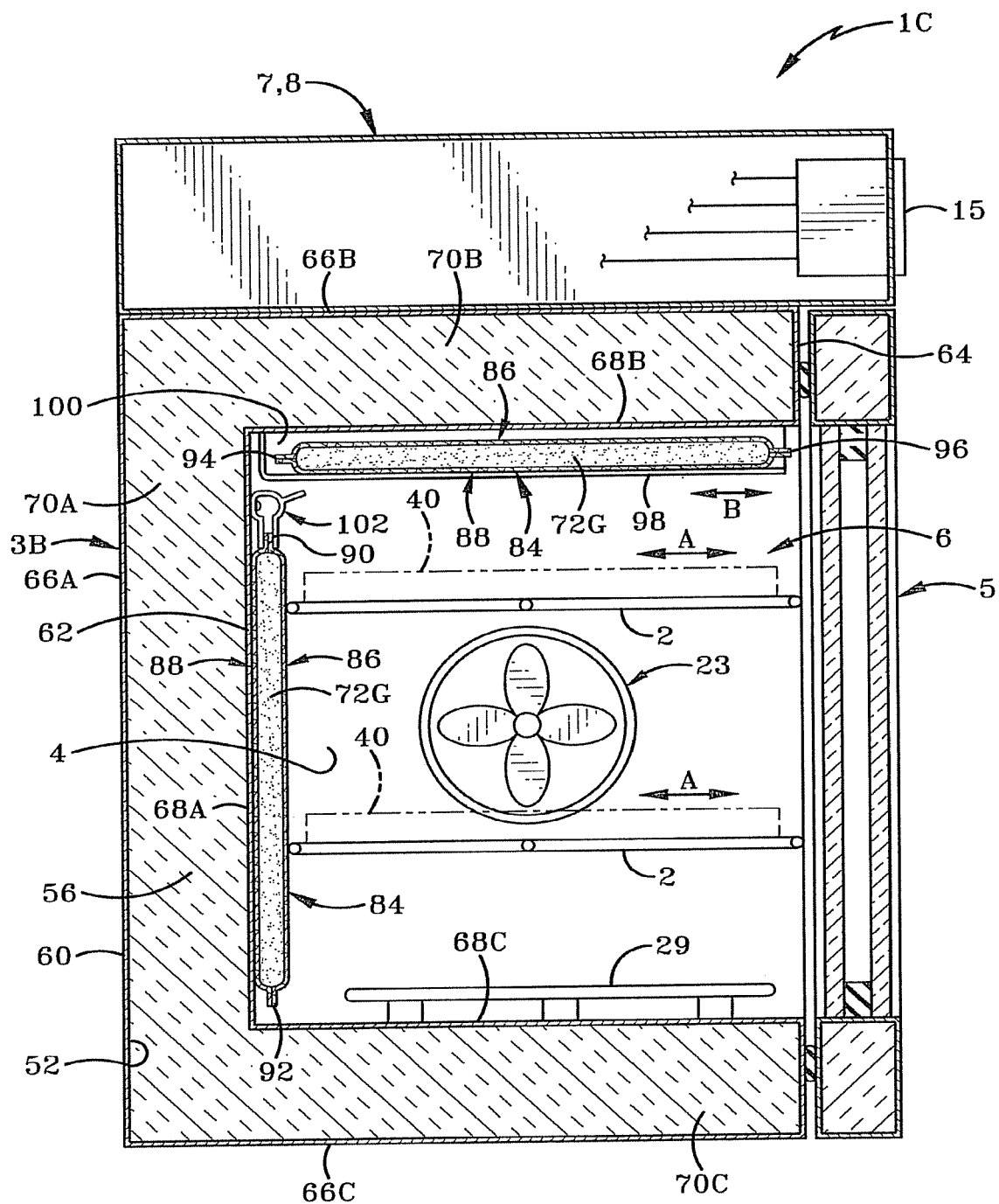
FIG. 8 is a sectional view similar to FIG. 7 of a fourth embodiment of the present invention also utilizing the phase change packets.
Figure 9:
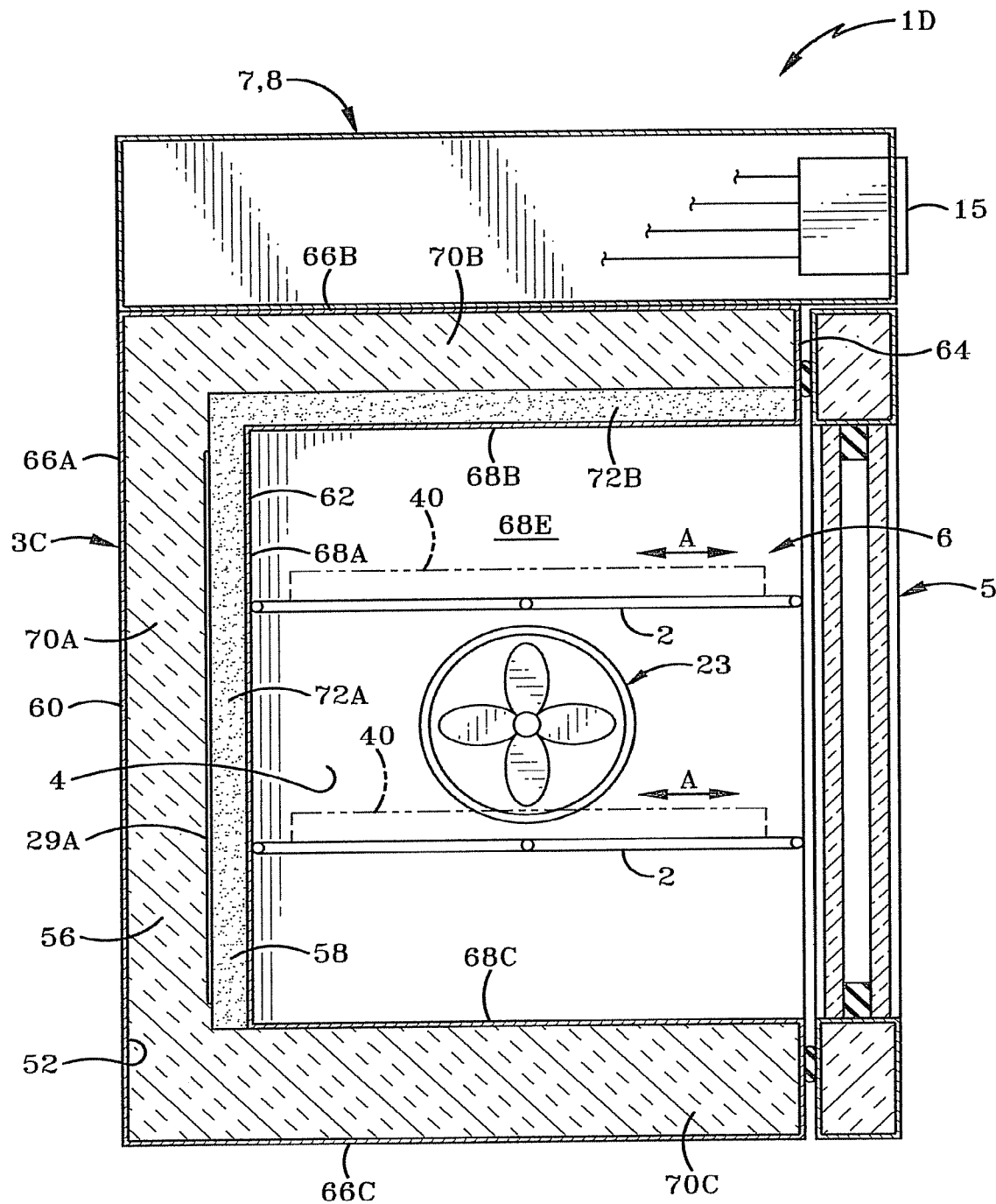
FIG. 9 is a sectional view similar to FIG. 2 of a fifth embodiment of the chamber of the present invention utilizing a heating element between the insulation and phase change material.
Figure 10:
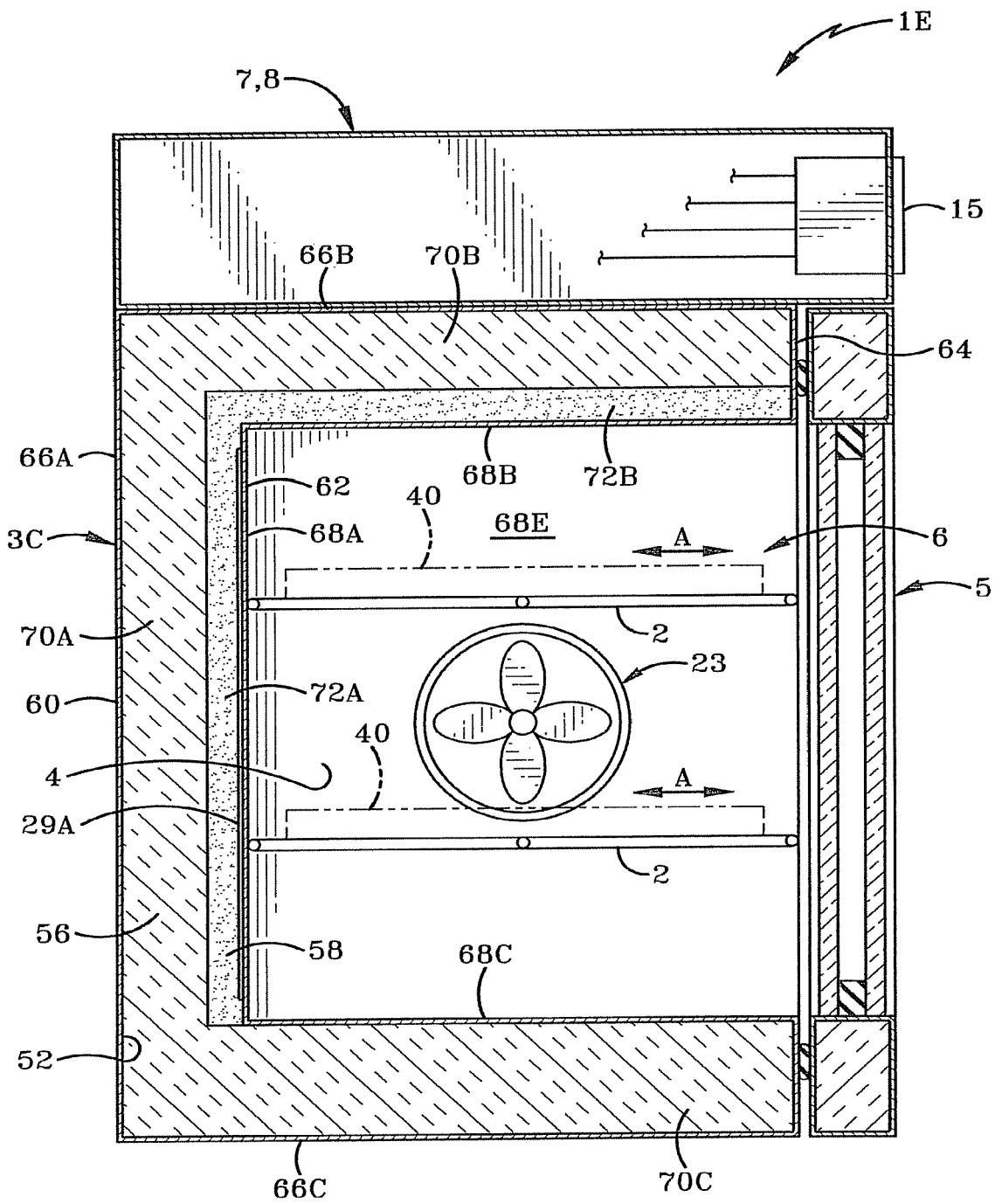
FIG. 10 is a sectional view similar to FIG. 9 of a sixth embodiment of the chamber of the present invention utilizing a heating element between the phase change material and the inner layer of the skin.
Figure 11:
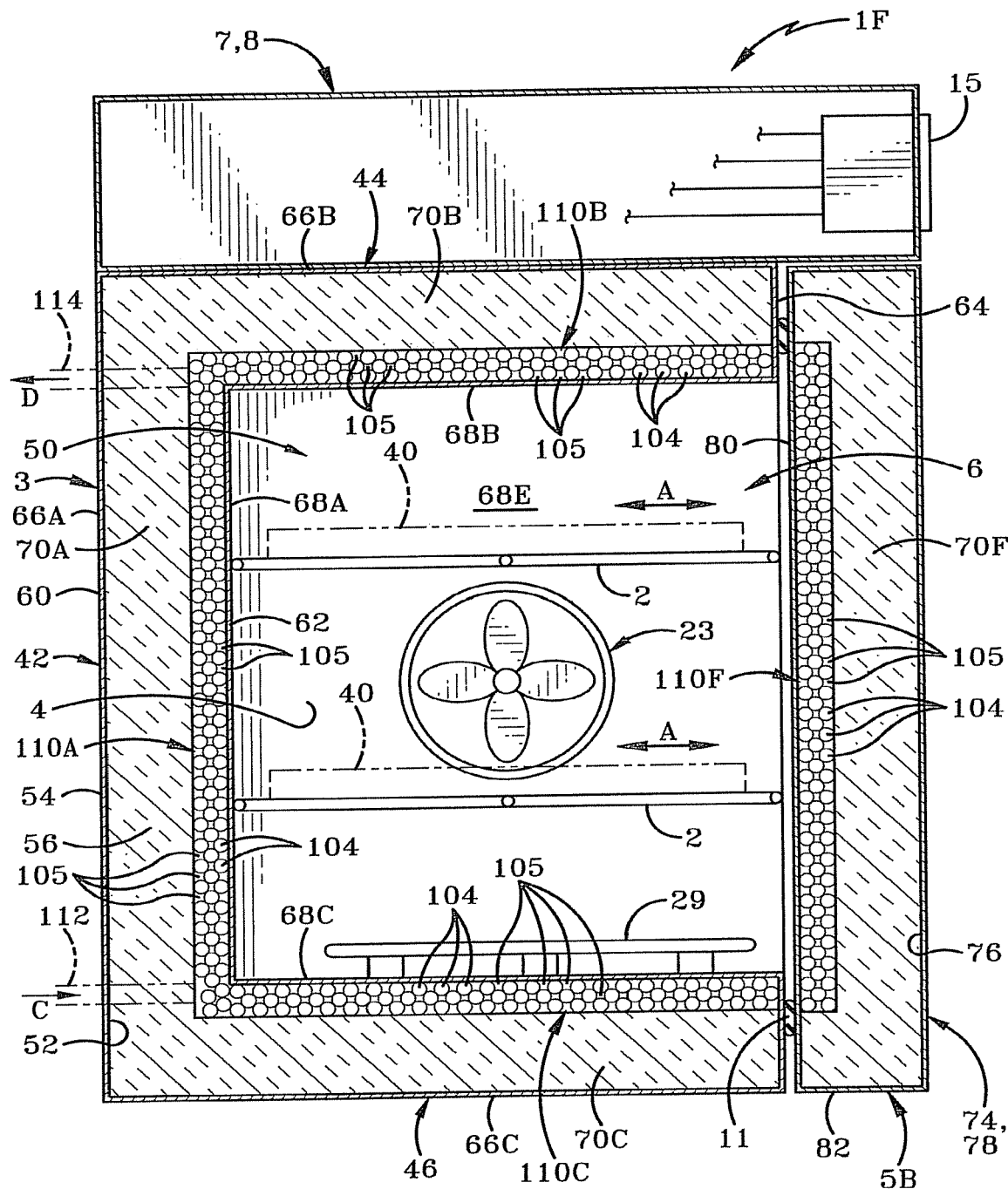
FIG. 11 is a sectional view similar to FIG. 5 of a seventh embodiment of the chamber of the present invention wherein the phase change material is contained within numerous encapsulated pellets which are within a liquid medium.
Figure 13:
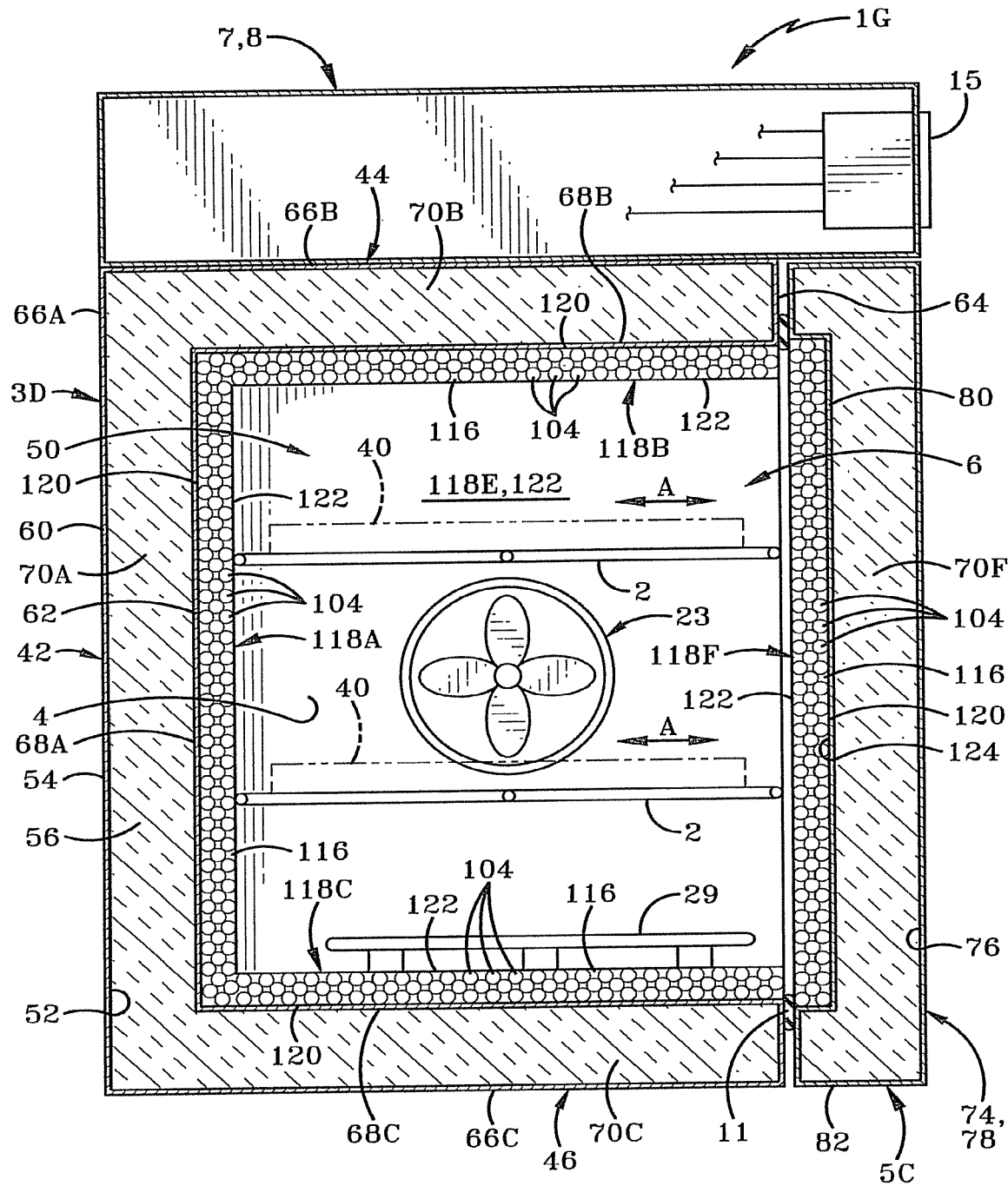
FIG. 13 is a sectional view similar to FIG. 12 of an eighth embodiment of the chamber of the present invention showing the phase change material within encapsulated pellets which are embedded in a solid matrix.
Figure 15:
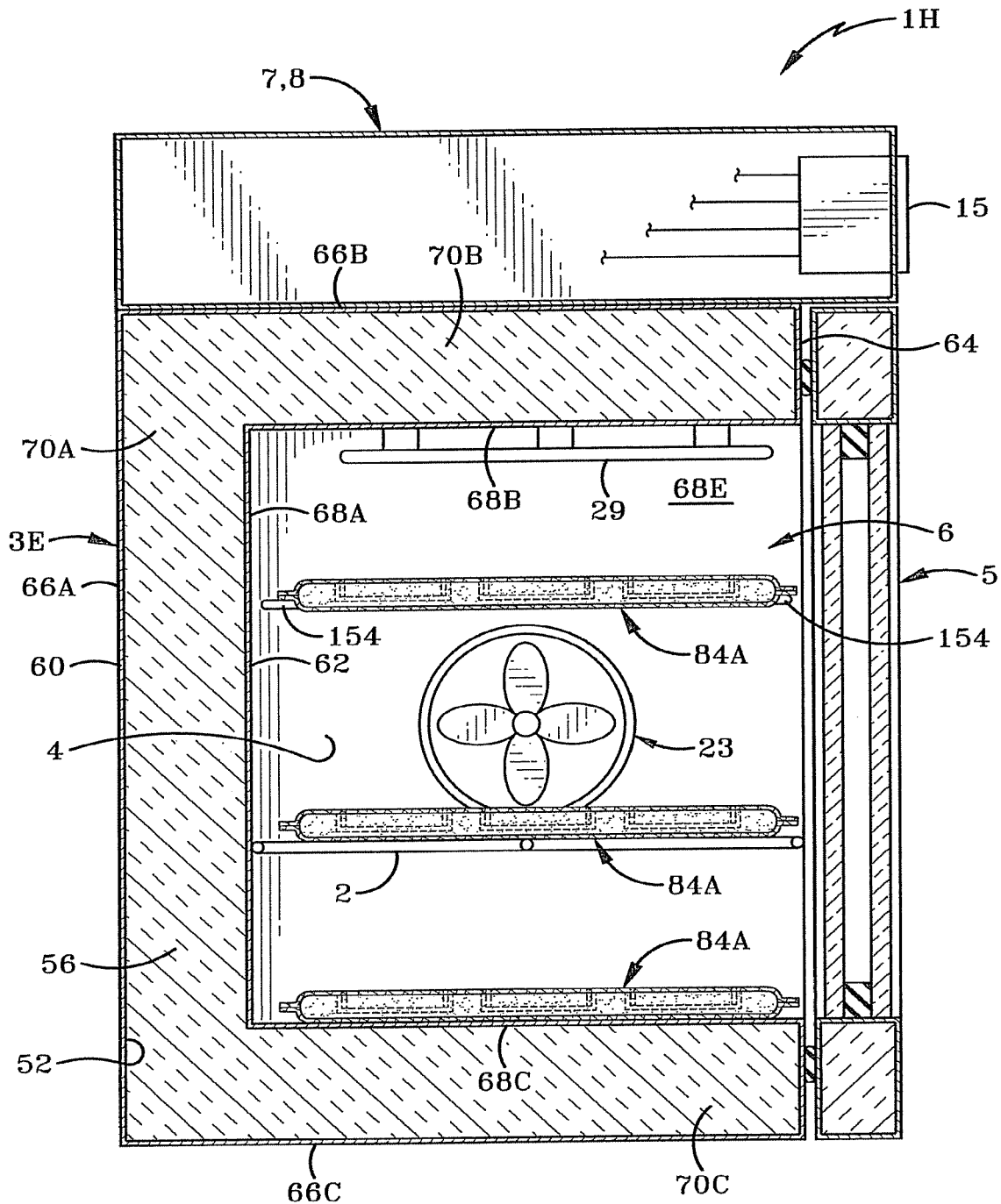
FIG. 15 is a sectional view similar to FIG. 7 of a ninth embodiment of the chamber of the present invention using the PCM packets or shelves shown in FIG. 14.

A first embodiment of the insulated enclosure or chamber of the present invention is shown generally at 1 in FIG. 1, with additional embodiments shown generally at 1A in FIG. 5, at 1B in FIG. 7, at 1C in FIG. 8, at 1D in FIG. 9, at 1E in FIG. 10, at 1F in FIG. 11, at 1G in FIG. 13, and at 1H in FIG. 15. Chamber 1 is configured to serve as an incubator, environmental chamber, oven, refrigerator or freezer. Chamber 1 includes a main body or container 3, a storage interior chamber 4 defined by container 3, a door 5 and a control assembly 7 secured to and seated atop container 3. Container 3 in the exemplary embodiment is in the form of a five-sided or five-walled box-like structure wherein the forward terminal ends of four of these walls define an entrance opening 6 (FIG. 2) of interior chamber 4. Upper and lower horizontal shelves 2 are disposed within interior chamber 4 extending between three of the walls of container 3 and suitably supported therein for supporting thereon one or more storage items 40 (dashed lines) to be stored in interior chamber 4 over a duration typically measured in hours, days, or weeks. Storage item 40 may, for example, be one or more petri dishes or other containers for growing cultures or for supporting other items which need incubation or heating in a controlled manner. Storage item 40 may also include the contents of a dish or container, such as a culture, and may include other components, some of which are discussed in greater detail further below. Item 40 may also be cooled in a controlled manner and frozen if desired. Insulated chamber is configured to heat and/or cool item 40 and/or to maintain item 40 within interior chamber 4 at a desired temperature, as described further below. Door 5 is hingedly attached to container 3 by hinges 9 to swing between open (FIG. 1) and closed (FIGS. 2, 4) positions. An annular sealing gasket 11 provides a seal between door 5 and container 3 when door 5 is closed, such that main body 3 and door 5 together form a six-sided or six-walled container or enclosure. Items 40 are removable from and insertable into (Arrows A in FIGS. 2, 5 7-11 and 13) interior chamber 4 through entrance opening 6 when door 5 is open.

Door 5 includes a transparent window 12 which may be double paned (FIG. 2) with two parallel panes 16 (typically made of glass) with an annular elastomeric seal 18 therebetween and in contact therewith to separate panes 16 by a space 20. Space 20 is defined by the inner perimeter of seal 18 and panes 16 and is filled with gas or under vacuum to help thermally insulate interior chamber 4 when door 5 is closed to cover entrance opening 6. Door 5 includes a rectangular annular wall 10 which surrounds window 12 along its outer edges and is hollow and typically includes a metal skin which defines a rectangular annular insulated fully enclosed door interior chamber or compartment 13 with thermal insulation 14 therein which nearly or completely fills compartment 13.

Control assembly 7 includes an enclosure or housing 8 on which is mounted a manual control interface 15 and which houses a temperature control unit 17, a humidity control unit 19 and a carbon dioxide control unit 21. Interface 15 is in electrical communication with control units 17, 19 and 21, and also with a fan assembly 23 within or in communication with interior chamber 4 and an electric power source 25 outside housing 8. Temperature control unit 17 is in electrical communication with a temperature sensor 27 within or bounding interior chamber 4 and with an electric heating unit or device in the form of a heating coil 29 within interior chamber 4. Temperature control unit 17 is also in electrical communication with a cooling device or refrigeration assembly 28 which includes internal heat-exchanging pipes 30 and external components 32 which typically include external heat-exchanging pipes, a compressor, and an expansion valve such that the refrigeration assembly provides a typical refrigeration cycle whereby the refrigerant within the coils is capable of providing active cooling within interior chamber 4 via the internal coils 30 therein. Cooling and heating devices 28 and 29 serve as electrically powered temperature-altering devices for altering the temperature of interior chamber 4, items 40 and other components within chamber 4 and portions of the walls defining chamber 4. Humidity control unit 19 is in electrical communication with a humidity sensor 31 within or bounding interior chamber 4 and with an actuator such as a solenoid of a water control valve 33 which is in fluid communication with a water source 35. Thus, humidity control unit 19 is operatively connected to interior chamber 4 to control the amount of humidity within chamber 4. Carbon dioxide control unit 21 is in electrical communication with a carbon dioxide sensor 37 and an actuator such as a solenoid of a carbon dioxide control valve 39 which is in fluid communication with a carbon dioxide source 41. Thus, carbon dioxide control unit 21 is operatively connected to interior chamber 4 to control the level of carbon dioxide within chamber 4.

Main body or container 3 is now described in greater detail. Container 3 has several generally rigid walls or sidewalls including a flat vertical rectangular back wall 42, flat rectangular horizontal top and bottom walls 44 and 46 secured respectively to the top and bottom of back wall 42 and extending forward therefrom, and flat vertical left and right side walls 48 and 50 secured respectively to the left and right sides of back wall 42 and extending forward therefrom. Left and right side walls 48 and 50 are also secured to and extend between the respective left and right ends of top and bottom walls 44 and 46. Walls 42-50 thus form a box or cup-shaped configuration defining interior chamber 4 such that walls 44-50 at their front ends define entrance opening 6. A fully enclosed sealed rectangular cup-shaped interior cavity or chamber 52 is formed within container 3 separate from interior chamber 4 and more particularly is defined by a substantially rigid skin 54 which is typically formed of metal although it may be formed of a plastic or other suitable material. Chamber 52 surrounds interior chamber 4 on five sides thereof. Wall or sidewall chamber 52 is sealed from external atmosphere and is nearly or completely filled by insulation 56 and a phase change material 58 (PCM), each of which is also in a substantially rectangular cup-shaped configuration corresponding to that of chamber 52. The phase change material 58 is disposed between the insulation and interior chamber 4 along the entire inner surface of insulation 56 and thus essentially completely surrounds interior chamber 4 on all five sides of container 3. Thus, each of walls 42-50 includes several layers or materials. Insulation 56 may be formed of a variety of insulation materials which remain in a solid state throughout the operation of the chamber and which are generally rigid or compressible. For example, insulation 56 may be fiberglass, styrofoam, or various types of foam boards or sheets, such as those formed from polystyrene, polyurethane, polyisocyanurate and the like. Some of these insulation boards are referred to commonly as polyiso boards. PCM 58 is discussed in greater detail further below. Although PCM 58 is shown on all five sides of container 3 entirely surrounding interior chamber 4, chamber 1 may also be formed with PCM 58 on only one, two, three or four sides of container 3 so that PCM 58 is adjacent chamber 4, but does not surround chamber 4.

Skin 54 includes a rectangular cup-shaped outer layer 60, a rectangular cup-shaped inner layer 62 and a rectangular annular front layer 64 which is substantially vertical and extends between the front of outer and inner layers 60 and 62. Outer layer 60 thus forms outer layers of each of the walls of container 3, namely vertical rear outer layer 66A of back wall 42, horizontal top outer layer 66B of top wall 44, horizontal bottom outer layer 66C of bottom wall 46, vertical left outer layer 66D of left side wall 48 and vertical right outer layer 66E of right side wall 50. Inner layer 62 similarly forms the inner layers of each of these walls, namely vertical front inner layer 68A of back wall 42, horizontal bottom inner layer 68B of top wall 44, horizontal top inner layer 68C of bottom wall 46, vertical right inner layer 68D of left side wall 48 and vertical left inner layer 68E of right side wall 50. Each of layers 66 and 68 is flat and rectangular.

Insulation 56 likewise makes up insulation layers of each of the five walls of container 3 which abut the respective outer layer 66 thereof and extend inwardly therefrom part of the way toward the respective inner layer 68 thereof. More particularly, insulation 56 includes a vertical flat rectangular insulation layer 70A of back wall 42 which abuts the front inner surface of outer layer 66A and extends forward therefrom, a flat rectangular horizontal insulation layer 70B of top wall 44 which abuts the lower inner surface of outer layer 66D and extends downwardly therefrom, a flat rectangular horizontal insulation layer 70C of bottom wall 46 which abuts the top inner surface of outer layer 66C and extends upwardly therefrom, a flat rectangular vertical insulation layer 70D of left side wall 48 which abuts the inner surface of outer layer 66D and extends inwardly to the right therefrom, and a flat rectangular vertical insulation layer 70E of right side wall 50 which abuts the left inner surface of outer layer 66E and extends inwardly to the left therefrom.

PCM 58 also forms respective PCM layers of each of the walls of container 3, namely a vertical flat rectangular PCM layer 72A of back wall 42 which extends between and is in contact with the front inner surface of insulation layer 70A and the rear surface of skin inner layer 68A, a flat rectangular horizontal PCM layer 72B which extends between and is in contact with the bottom inner surface of insulation layer 70B and the top surface of inner layer 68B, a flat rectangular horizontal PCM layer 72C which extends between and is in contact with the upper surface of insulation layer 70C and the lower surface of inner layer 68C, a vertical flat rectangular PCM layer 72D which extends between and is in contact with the inner surface of insulation layer 70D and the left surface of inner layer 68D, and a flat rectangular vertical PCM layer 72E which extends between and is in contact with the left inner surface of insulation layer 70E and the right surface of inner layer 68E. Each PCM layer 72 is thus disposed within a cavity or portion of interior chamber 52 between the corresponding inner layer of the skin and layer of insulation 70.

Chamber 1A (FIG. 5) is similar to chamber 1 except that it includes a door 5A which is somewhat different than door 5 although both doors are substantially rigid and serve as a wall or sidewall of the chamber 1 or 1A. Unlike door 5, door 5A does not include a transparent window which allows someone to view the contents of interior chamber 4 from outside the chamber without opening the door. Instead, door 5A is opaque and has a configuration similar to one of the walls of container 3 and is thus made of several layers. In particular, door 5A includes a substantially rigid skin 74 which is relatively thin and typically formed of metal and defines a fully enclosed vertical rectangular interior cavity or chamber 76 which is separate from chambers 4 and 52, which is sealed from external atmosphere and in which are disposed an insulation layer 70F and a PCM layer 72F. Skin 74 includes outer and inner vertical rectangular layers 78 and 80 and a rectangular annular perimeter layer 82 which extends between and is secured to the respective outer perimeters of outer and inner layers 78 and 80 such that layers 78-82 define therewithin chamber 76. Insulation layer 70F extends from the top to the bottom and from the left side to the right side of interior chamber 76. Insulation layer 70F also abuts the inner surface of outer layer 78 and extends inwardly and rearwardly therefrom and may contact the front inner surface of inner layer 80 along its outer perimeter although insulation layer 70F only extends part of the way towards inner layer 80 along a rectangular portion of door 5A which is directly in front of entrance opening 6. PCM layer 72F is a flat vertical rectangular layer which extends between and abuts the front surface of inner layer 80 and the rear surface of insulation layer 70F such that when door 5A is closed, PCM layer 72F entirely covers or spans the entrance opening 6 of interior chamber 4. PCM layer 72F is thus disposed within a cavity or portion of the sidewall or door interior chamber 76 defined between inner layer 80 and insulation layer 70F. PCM layer 72F is intended to be permanently disposed within chamber 76 and is thus not removable therefrom, just as the PCM layers 72A-E are not removable from interior chamber 52 of container 3.

Figure 6:
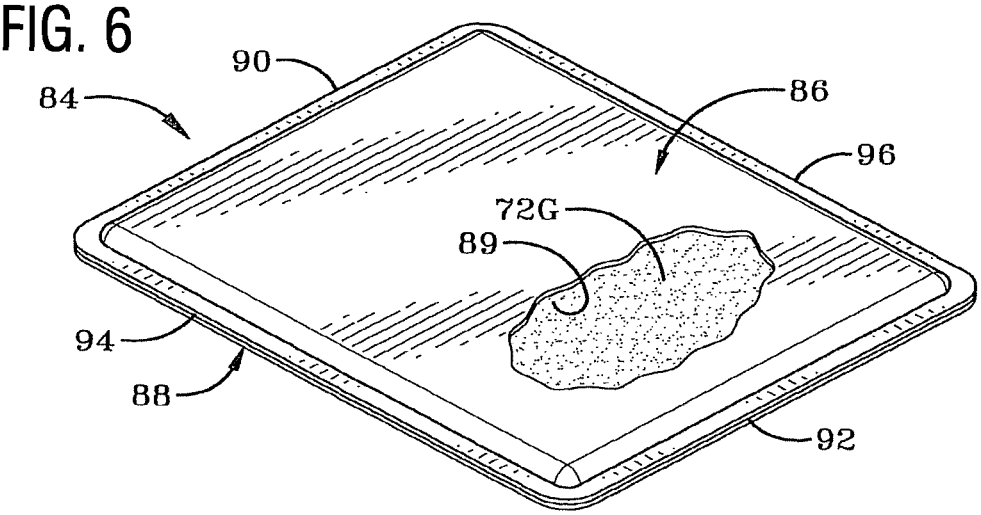
FIG. 6 is a perspective view with portions cut away of the removable and repositionable phase change material packet or wall of the present invention.

FIG. 6 illustrates a removable PCM packet 84 which is typically easily carried by one person and otherwise manipulated with one or two hands for use with chambers configured to receive packet 84. Packet 84 includes first and second substantially flat rectangular walls 86 and 88 which together form an outer skin and overlay one another such that their outer perimeters are superimposed and in contact with one another while the vast majority of walls 86 and 88 are spaced from one another to define therebetween a flat rectangular interior cavity or chamber 89 which receives therein a flat rectangular PCM layer 72G which nearly or completely fills chamber 89. Walls 86 and 88 are preferably formed of a substantially rigid thermally conductive material, such as a metal. Aluminum, stainless steel and copper are well suited for this purpose. However, walls 86 and 88 may be formed of a plastic or other suitable material. Packet 84 has first and second opposed straight parallel end edges 90 and 92, and first and second straight parallel opposed side edges 94 and 96 which extend respectively between end edges 90 and 92 so that edges 90-96 form a rectangular configuration along the outer perimeters of walls 86 and 88. Walls 86 and 88 are sealed to one another along each of edges 90-96 so that interior chamber 89 is fully enclosed and sealed from external atmosphere.

Chamber 1B is shown in FIG. 7 and utilizes removable PCM packets 84. Chamber 1B is similar to chambers 1 and 1A and is shown with door 5 although a door such as door 5A may also be used. Chamber 1B includes a container 3A which is similar to container 3 except that the insulation entirely or nearly entirely fills the interior chamber 52 since the PCM material is provided in packets 84 instead of within interior chamber 52. Thus, for example, the insulation layer 70A in the back wall of container 3A extends all the way from the front surface of outer layer 66A to the back surface of inner layer 68A. Similarly, insulation layer 70B extends continuously from the bottom surface of outer layer 66B to the top surface inner layer 68B, and insulation layer 70C extends all the way from the bottom surface of inner layer 68C to the top surface of outer layer 66C. The insulation layers in the two side walls of container 3A also extend all the way between the respective inner and outer layers thereof.

As shown in FIG. 7, the heating element 29 of chamber 1B is mounted on the top wall of container 3 within interior chamber 4 adjacent the top thereof. FIG. 7 further illustrates three of the removable PCM packets 84 within interior chamber 4. One of packets 84 is seated on top inner layer 68C of the bottom wall of container 3, which thus serves as a supporting structure or permanent shelf for the lower packet 84. Chamber 1B further includes a pair of horizontal trays 98 which respectively hang downwardly from the wire or other type shelves 2 such that each tray and the respective shelf are adjacent one another and define therebetween a respective rectangular flat horizontal packet-receiving space 100 for removably inserting therein a respective packet 84 through a front entrance opening of a respective space 100. Thus, the lowermost packet 84 is directly below the other two packets as well as directly below the two shelves and trays, and spaced downwardly from the lower tray. The middle packet 84 is thus seated atop the lower tray 98 below and adjacent the lower removable shelf 2. Similarly, the top or upper packet 84 is seated atop the upper tray 98 below and adjacent the removable upper shelf 2. In addition, the upper tray 98 is spaced upwardly from the lower shelf 2 so that a portion of interior chamber 4 is defined between the top of the lower shelf 2 and the bottom of tray 98 inasmuch as the upper tray 98 and the corresponding upper packet 84 is spaced upwardly from the lower shelf 2. This portion of interior chamber 4 receives petri dishes or other items 40 which are seated on the lower shelf 2 so that the temperature of item 40 and the environment in interior chamber 4 surrounding item 40 may be controlled. Items 40 are thus adjacent, above and out of contact with the respective packet 84 during the process of temperature and other environmental control in interior chamber 4. Similarly, interior chamber 4 includes an upper portion above the upper shelf 2 also configured to receive items 40, which are likewise adjacent, above and out of contact with the upper packet 84 during the process of thermal and other environmental control within interior chamber 4. As previously noted, each packet 84 may be inserted and removed from its respective space 100 or from atop the bottom wall (Arrows B in FIGS. 7, 8) through the entrance opening 6 when door 5 is open. Trays 98 serve as PCM packet shelves. However, PCM packets 84 may also be seated on shelves 2 or another support so that items 40 may be seated directly on packets 84.

Chamber 1C (FIG. 8) is similar to the previous chambers and includes a container 3B which is similar to but somewhat modified from the earlier containers. The insulation within interior chamber 52 of container 3B is the same as that described with reference to the insulation within container 3A of chamber 1B. As shown in FIG. 8, the heating element 29 is mounted adjacent and above the bottom wall of the container within interior chamber 4 in the same manner as with chamber 1. Chamber 1C illustrates the use of two PCM packets 84 in a different orientation than that shown with chamber 1B. A tray 98 is mounted on the top wall of container 3B within the upper portion of interior chamber 4 so that the upper PCM packet may slide horizontally (Arrow B in FIG. 8) to be inserted or removed from the space 100 above tray 98 and below and adjacent the top wall of container 3B. The other packet 84 is positioned in a vertical orientation behind removable shelves 2 abutting or adjacent the front inner surface of inner layer 68A of the back wall of container 3B. More particularly, a clip 102 is secured to the back wall adjacent the top wall of the container and clips or clamps the first end edge 90, which serves as the top of packet 84 in the vertical orientation in order to suspend packet 84 in this rearward position. As will be appreciated, any suitable mechanism may be used in order to secure packet 84 in its hanging position or a vertical position closely adjacent the back insulating wall. PCM packets 84 of insulated chamber 1B and 1C are positioned so that they do not hinder the insertion and removal of items 40 from interior chamber 4, that is, items 40 may be inserted and removed without moving PCM packets from their respective positions within chamber 4. In addition, packets 84 are configured so that PCM 72G (like the non-removable PCM 72 of chamber 1) is not visible to the end user of the insulated chambers 1B and 1C. Moreover, PCM packets 84 are configured and positioned in chamber 4 so that the space normally reserved for items 40 on shelves 2 (i.e., without the use of packets 84 or trays 98) is not substantially reduced, and in most cases the reduction in available space for items 40 is not significant enough to have any real impact. Thus, the items 40 normally placed in a chamber 4 of a given size may still be placed therein with the addition of trays 98 and/or packet(s) 84. Although not shown, it is contemplated that a packet 84 may be positioned in a space behind or adjacent a "false" wall within chamber 4 such that the packet is hidden and whereby heat transfer to and from the packet is largely by convection. For example, such a false wall may be situated in front of the vertical packet 84 shown in FIG. 8.

Figure 2:
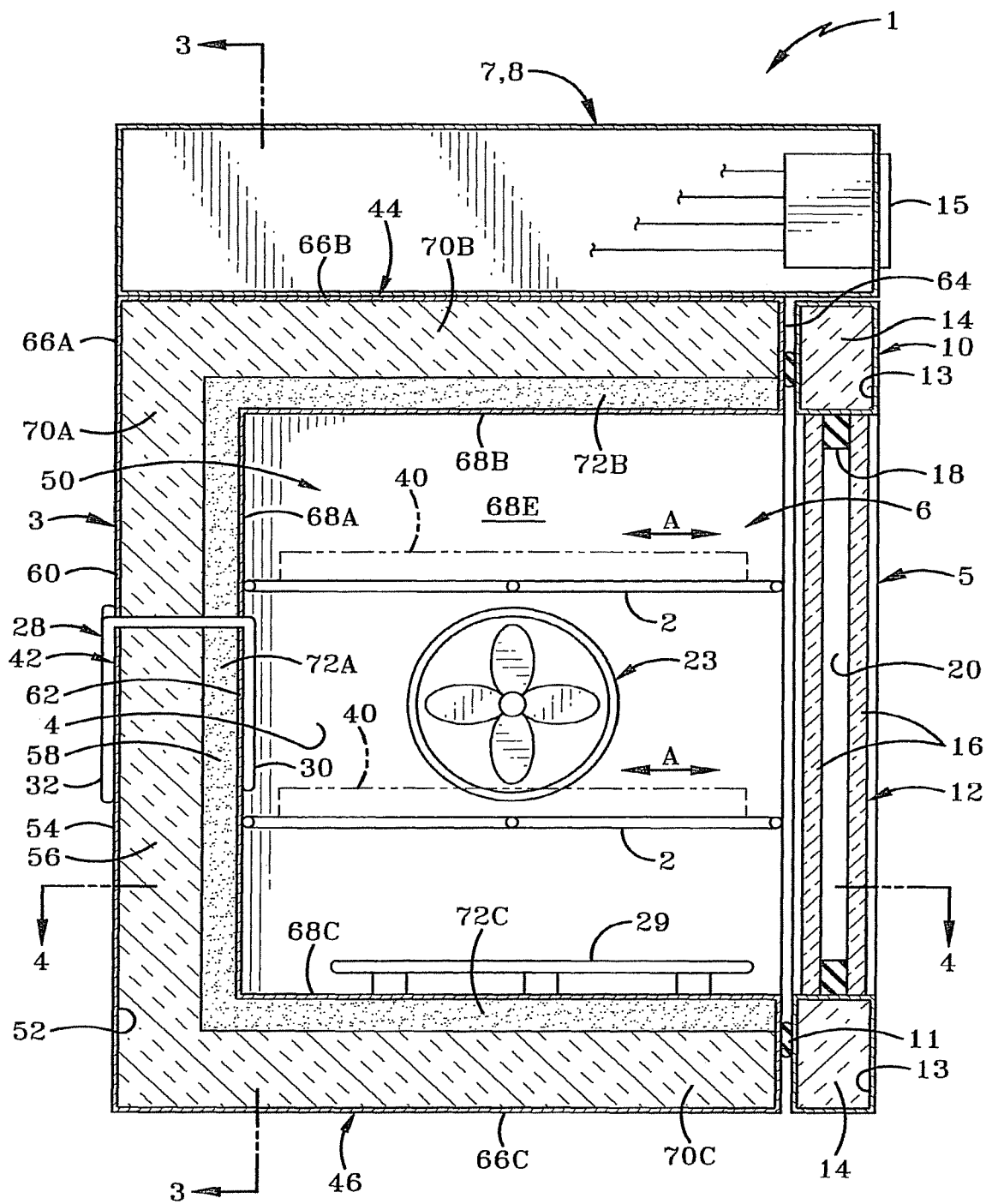
FIG. 2 is a sectional view taken on Line 2-2 of FIG. 1.
Figure 3:
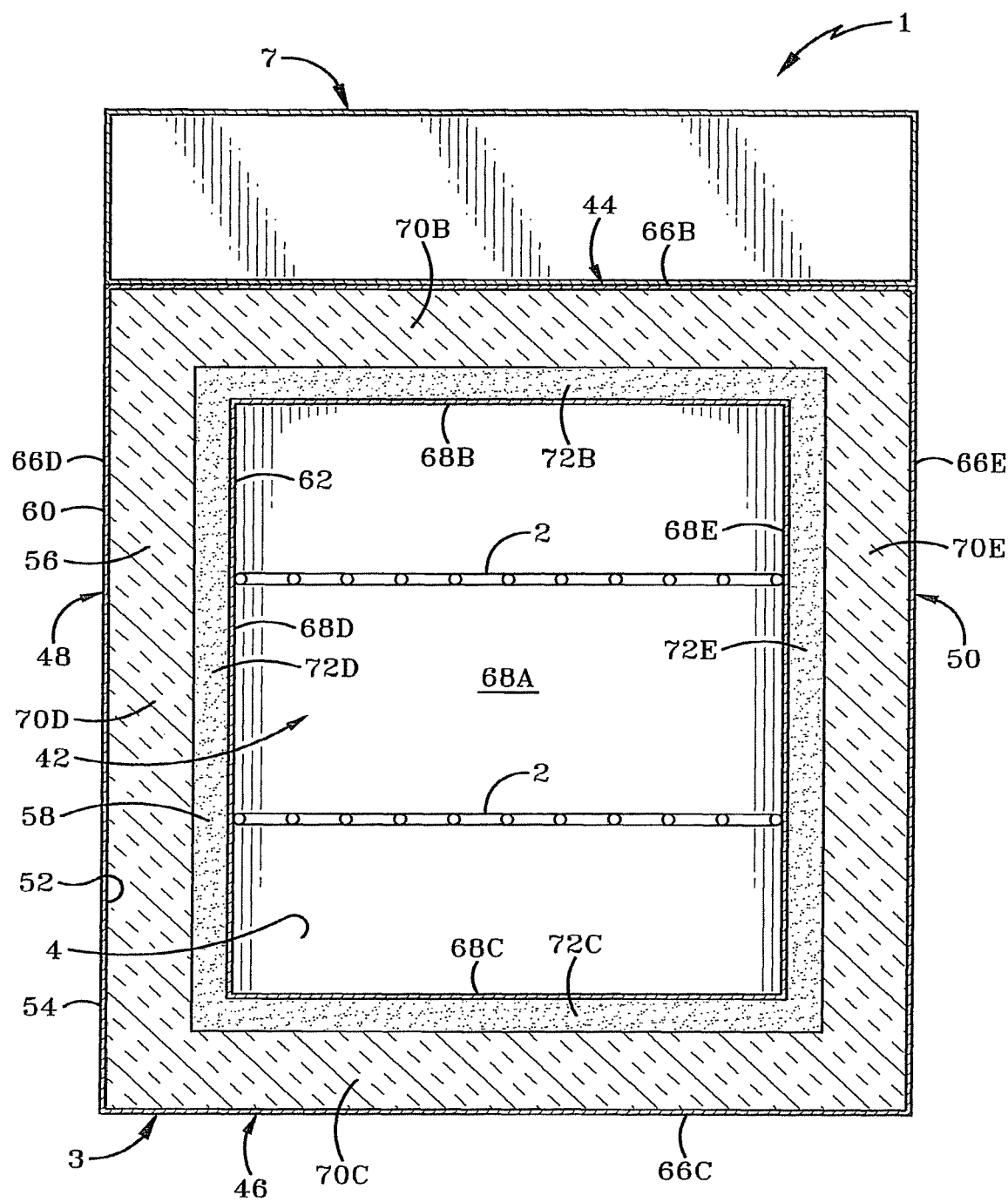
FIG. 3 is a sectional view taken on Line 3-3 of FIG. 2.

Chamber 1D (FIG. 9) is similar to the previous chambers and includes a modified container 3C such that the interior chamber 52 contains insulation, PCM, and a heating element 29A sandwiched therebetween. The insulation layer 70C of chamber 1D is substantially the same as that described with regard to the chambers 1B and 1C in FIGS. 7 and 8. Similarly, the insulation in the left and right side walls of container 3C completely or nearly fills the portions of chamber 52 within the respective left and right side walls of container 3C. The insulation layers 70A and 70B of container 3C are substantially the same as those of chamber 1, as illustrated in FIGS. 2 and 3. In addition, the PCM layers 72A and 72B within container 3C are substantially the same as that shown and described with reference to FIGS. 2 and 3 of chamber 1. In chamber 1D, only these two PCM layers 72A and 72B are used such that the bottom wall and left and right side walls of container 1D do not include such PCM layers. As FIG. 9 illustrates, interior chamber 4 is free of a heating element such as heating element 29 of the previous embodiments. Instead, heating element 29A is sandwiched between insulation layer 70A and PCM layer 72A and is thus substantially vertically oriented and in contact with each of said layers. Element 29A is thus entirely external to interior chamber 4.

Chamber 1E (FIG. 10) is similar to chamber 1D except that it includes a heating element 29A which is sandwiched between PCM layer 72A and inner layer 68A. Element 29A is thus in contact with the rear surface of layer 68A and the front surface of PCM layer 72A.

Figure 12:
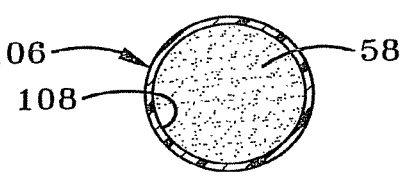
FIG. 12 is a sectional view of one of the encapsulated pellets.

Chamber 1F (FIG. 11) is similar to chamber 1A (FIG. 5) except that the various layers 72 of PCM 58 are replaced by numerous encapsulated PCM pellets 104 and a liquid medium 105 in which the pellets 104 are disposed. As shown in FIG. 12, each pellet 104 includes a solid capsule 106 having an inner surface which defines an interior chamber 108 or an enclosure which is sealed from the external atmosphere or environment by the solid skin or capsule 106. Interior chamber 108 is nearly or completely filled with PCM 58. As shown in FIG. 11, the mixture of pellets 104 and medium 105 form layers 110 which include a substantial amount of PCM 58 and are analogous to layers 72. While layers 110 may be on all sides of interior chamber 4, FIG. 11 shows only layers 110A, 110B, 110C and 110F, which are respectively analogous to layers 72A, 72B, 72C and 72F. Typically, pellets 104 are packed in as tightly or nearly as tightly as they can within the portion of interior chamber 52 defined between insulation 56 and inner layer 62 of skin 54. Pellets 104 are similarly packed into the portion of interior chamber 76 of the door between the insulation layer 70F and inner layer 80 of skin 74. Pellets 104 define therebetween interstitial spaces which are typically completely or nearly filled by liquid medium 105. Although in the exemplary embodiment, medium 105 is in a liquid form, it may also be in a gaseous form. In any case, the interior chamber 52 is completely or nearly filled by insulation 56, pellets 104 and medium 105. Similarly, the interior chamber 76 of the door is nearly or completely filled with insulation 70F, pellets 104 and medium 105.

As shown in dashed lines in FIG. 11, chamber 1F may include an inlet 112 and an outlet 114 communicating with the portion of interior chamber defined between insulation 56 and inner layer 62 of skin 54 such that a liquid or a mixture of pellets 104 and liquid medium 105 may be pumped or otherwise moved into this portion of the interior cavity via inlet 112 (arrow C) and out of this portion of the interior cavity through outlet 114 (arrow D). The provision of an inlet and an outlet is one manner of filling this portion of the interior chamber 52 with pellets 104 and medium 105, and also would allow for the pellets and medium to be removed via outlet 114 and, if desired, replaced with another set of pellets and liquid medium in which the PCM 58 of the pellets has a different melting or freezing temperature than that of the original pellets. It is noted that liquid 105 may be a phase change material which serves in the same fashion as PCM 58, or it may remain in a liquid state within the operational parameters of chamber 1F. The illustration with the use of inlet 112 and outlet 114 may represent the type of insulated chamber which uses a water jacket. Thus, instead of using the water jacketed insulated chamber in the standard manner, pellets 104 and liquid medium 105 may instead be used to fill the interior chamber of the water jacket in order to utilize the advantage of PCM 58 of the present invention.

Chamber 1G (FIG. 13) is similar to chamber 1F in that it also utilizes PCM pellets 104. However, instead of pellets 104 being disposed within liquid medium 105, pellets 104 of chamber 1G are embedded in a solid matrix 116. More particularly, the matrix 116 and embedded pellets 104 form respective flat rectangular layers 118 which are analogous to PCM layers 72A-F and layers 110 such that each of the layers is flat and rectangular and either horizontal or vertical as previously discussed with respect to layers 72. FIG. 13 shows specifically layers 118A-C, 118E and 118F. However, unlike layers 72 and layers 110, layers 118 are in the exemplary embodiment not within the interior chamber 52 defined by skin 54 of such chambers as chamber 1, 1A and 1F. Although layers 118 could be positioned within chamber 52 in the analogous positions of layers 72 and 110, the use of layers 118 illustrates one manner of forming layers comprising PCM 58 wherein the layers are external to interior chambers 52 and 76. Thus, chamber 1G may include a container 3D and a door 5C each of which has a somewhat different configuration than those of the previous embodiments. Container 3D retains skin 54 and its various layers to define there within the interior chamber 52. However, insulation 56 itself either completely or nearly fills interior chamber 52. FIG. 13 shows that inner layers 68 of skin 54 are positioned closer to the corresponding outer layers 68 such that outer layers 66 abut the outer surface of insulation 56 and the inner layer 68 abut the inner surface of insulation 56. Thus, insulation 56 in FIG. 13 appears to have the same thickness as insulation 56 in FIG. 11. However, the inner and outer layers 66 and 68 may also be spaced apart from one another as in the previous embodiments such that insulation 56 still fills the entire chamber 52 and is thicker, as shown in FIG. 7.

Each of layers 118 has an outer surface 120 and an inner surface 122. Each outer surface 120 of a given layer 118 which is part of container 3D abuts an inner surface of a corresponding inner layer 68 so that each layer 118 extends inwardly therefrom to inner surface 122. Thus, for instance, outer surface 120 of layer 118A is vertical and abuts the vertical inner surface of back inner layer 68A and extends inwardly therefrom to vertical surface 122 of layer 118A. The outer surface 120 of layer 118B serves as a top surface which thus abuts the inner or bottom surface of top inner layer 68B so that layer 118B extends downwardly therefrom to the horizontal inner or bottom surface 122 thereof. The outer surface 120 of layer 118C thus serves as a bottom horizontal surface from which layer 118C extends upwardly to the inner or top horizontal surface 122 thereof. The left and right walls of container 3D are formed in a similar manner to the back wall thereof such that the corresponding layer 118 is vertical, and the inner and outer surfaces 120 and 122 of the corresponding vertical layers 118 (layer 118E shown in FIG. 13) are vertical and oriented such that the outer layer 120 abuts the corresponding inner layer 68 and extends inwardly therefrom to the vertical inner surface 122. Thus, the inner surfaces 122 of the layers 118 define interior chamber 4, unlike the earlier embodiments in which the inner layers 68 of skin 54 defined interior chamber 4.

Although door 5C is similar to the doors of the earlier embodiments, it also differs somewhat in that inner layer 80 defines a vertical flat rectangular recess 124 in which layer 118F is received with its vertical outer or front surface 120 abutting the vertical inner surface of layer 80 and extending forward therefrom to the flat vertical inner or rear surface 122, which bounds interior chamber 4 when door 5C is closed. Although layer 118F is shown disposed in recess 124, a layer similar to 118F may be mounted on a door without such a recess and thus project forward beyond the forward most portion of the inner skin.

In the exemplary embodiment, solid matrix 116 is typically formed of a cured resin. Thus, during formation of layers 118, the original material which ultimately becomes matrix 116 is a liquid resin or in liquid form and thus cures to form the solid resin. In one embodiment, pellets 104 are mixed into a paint, which can then be painted onto any given surface, such as the inner layer 62 and the inner layer 80 and then allowed to dry. Paints typically contain a resin and a solvent, such that when the solvent dries, the resin is allowed to cure by chemical reaction. Some paints are also thermosetting, meaning that they are also heated in order to cure the resin. In another embodiment of solid matrix 116, the resin may not include a solvent which needs to dry in order to cure. For example, some resins are simply heat cured from a liquid state to a solid state without or with extremely minimal evaporation of components making up the liquid resin. Other liquid resins may be light cured in order to reach the solid state.

Thus, the layers 118 may be formed in several different ways. Where the matrix and its liquid form is a paint, the paint with pellets 104 mixed into it may simply be painted onto a given desired surface and allowed to dry. Another option is to pour a given liquid resin with the pellets 104 mixed therein into a cavity or recess such as recess 124 (such as when door 5C is laid horizontal with the recess 124 facing upwardly), and either allowed to dry, as with the paint, or cured by heat, light or any other suitable method in order to cure the resin within the recess. Alternately, any of the layers 118 may be independently formed in a mold cavity and subsequently mounted in the positions shown in FIG. 13 by any suitable mechanism. For instance, the bottom layer 118C may simply be laid atop the inner layer 68C, or may be adhered with a glue or another adhesive thereto. The other layers 118 may similarly be adhered by a glue or an adhesive or so forth. Further, the various layers 118 of container 3D may be formed as a single cup-shaped piece. Such formations may be done in a separate mold, or may use the inner layer 62 of skin 54 to define a portion of the mold. Matrix 116 may have varying degrees of thermal conductivity. The thermal conductivity may be enhanced by incorporating metal chips or other materials which are highly thermally conductive into the liquid resin during formation of the layers 118.

Figure 14:
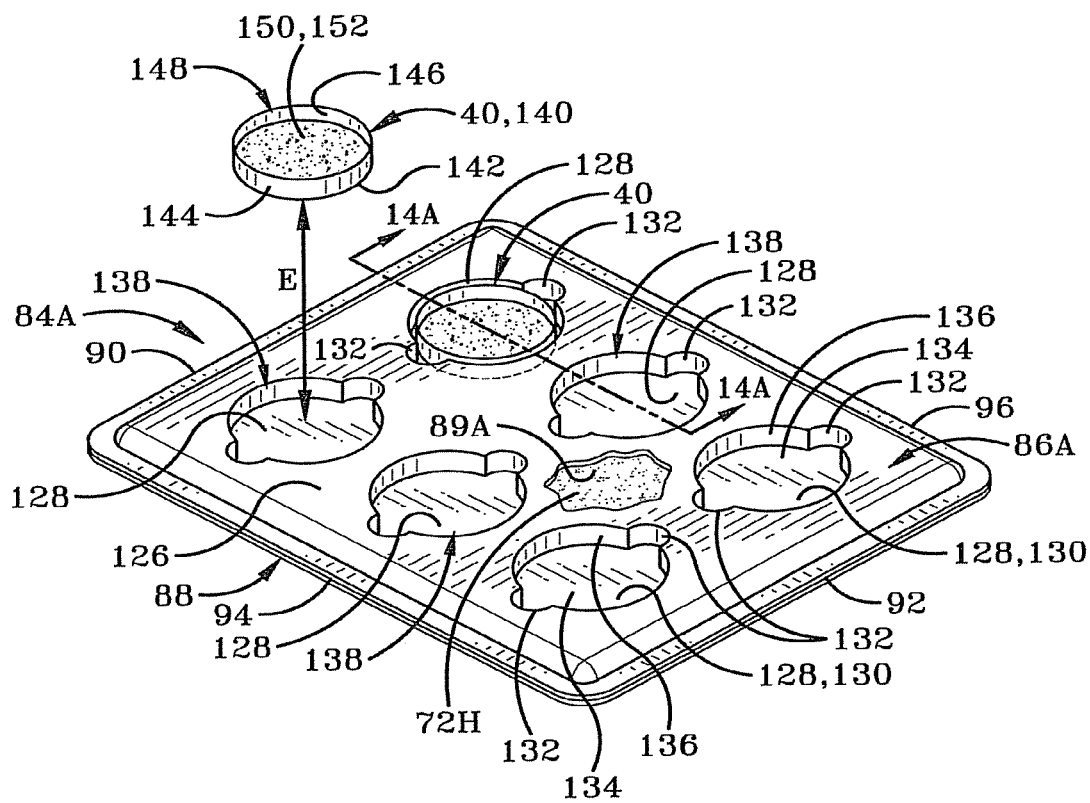
FIG. 14 is a perspective view of a PCM packet or shelf having recesses formed therein for receiving respective storage items.

FIG. 14 shows another PCM packet or shelf 84A which is similar to packet 84 shown in FIG. 6. Shelf 84A thus includes generally flat rectangular bottom wall 88 and a generally flat rectangular top wall 86A which define therebetween an interior chamber 89A which is filled with a layer 72H of PCM. PCM layer 72H typically completely or nearly fills interior chamber 89A. It is noted that PCM layer 72H of packet 84A or PCM layer 72G of packet 84 (FIG. 6) may be replaced with pellets 104, along with a gas or liquid medium 105 (FIG. 11) or embedded in solid matrix 116 (FIG. 13). Walls 86A and 88 are formed of the same materials as previously described with regard to packet 84, and are joined to one another to form end edges 90 and 92, and side edges 94 and 96. Unlike wall 86 of packet 84, which is substantially flat in a continuous manner from adjacent edge 90 to adjacent edge 92 and from adjacent edge 94 to adjacent edge 96, wall 86A includes an upper flat portion 126 which extends from adjacent edge 90 to adjacent edge 92 and from adjacent edge 94 to adjacent edge 96, but is interrupted by a plurality of recesses 128 extending downwardly therefrom. In the exemplary embodiment, packet 84A includes six recesses 128 although the number may vary depending on the size of the packet and the specific need. Although recesses 128 may be of any desired shape, each recess 128 is shown with a circular central portion 130 and a pair of opposed finger receiving portions 132 which extend laterally outwardly from central portion 130 on opposite sides thereof and away from one another. The bottom of each recess 128 is defined by a flat horizontal recessed wall 134 which is spaced downwardly from upper flat portion 126. An annular side wall 136 at its lower end is rigidly secured to and extends upwardly from the outer perimeter of recessed wall 134 to a rigid connection at its upper end to upper flat portion 126, whereby each recessed wall 134 and the corresponding side wall 136 defines the corresponding recess 128. Each recess 128 has a top entrance opening 138 through which a given storage item 40 may be downwardly inserted and upwardly removed, as indicated at arrow E in FIG. 14.

With continued reference to FIG. 14, the specific storage item 40 includes a container or petri dish 140 having a flat circular bottom wall 142 and a circular annular side wall 144 rigidly secured to and extending upwardly from the bottom wall 142 to define there within a cylindrical cavity 146 with a top entrance opening 148. Cavity 146 is thus configured to receive various contents via entrance opening 148 and/or have the contents removed thereby. In the exemplary embodiment, item 40 includes the contents, which are in the form of a culturing medium 150 with living cells 152 to be grown or cultured thereon.

Figure 14A:
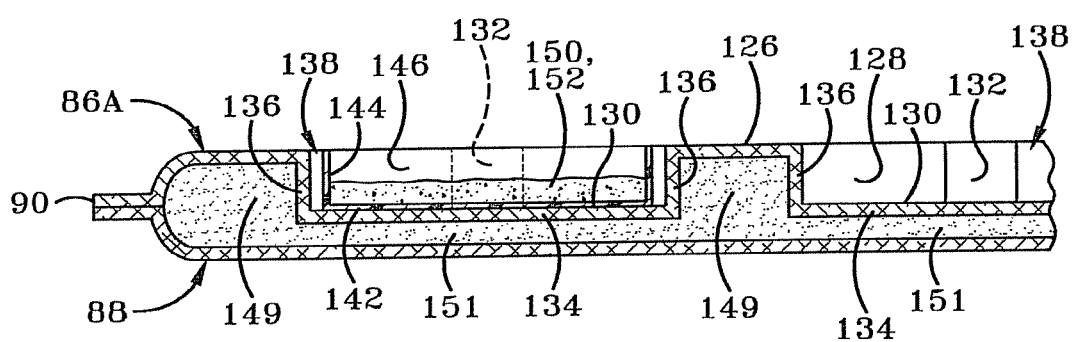
FIG. 14A is a sectional view taken on line 14A-14A of FIG. 14.

The sectional view of FIG. 14A illustrates the relative positions of the petri dish 140 and its contents to the corresponding recess 128 and various components of the packet 84A, including the PCM. The PCM of layer 72H includes a lateral portion or portions 149 which may also be referred to as a recess-surrounding portion. The PCM of layer 72H also includes respective sub-recess portions 151 which are located directly below the corresponding recess 128 and recessed wall 134. The lateral portions 149 extend laterally outwardly from annular side wall 136 in all directions so that this portion of the PCM, as viewed from above, surrounds the corresponding annular side wall 136, as well as the bottom wall 134, recess 128, and when petri dish 140 is disposed within 128, also the bottom wall 142 thereof, at least a portion of side wall 144, and all or part of medium 150 and cells 152. Portions 149 have a top surface which abuts the bottom surface of upper flat portion 126 whereby the PCM of layer 72H extends from below recessed wall 134 and the bottom of petri dish 140 to above recessed wall 134, bottom wall 142, most or all of side wall 144 and all or part of medium 150 and cells 152. In the exemplary embodiment, bottom wall 142 of dish 140 is seated on horizontal flat recessed wall 134 with annular side wall 144 abutting or closely adjacent annular side wall 136, which typically has a substantially similar shape as side wall 144 as viewed from above so that the petri dish side wall and the contents of the dish are adjacent portions 149 of PCM. In the exemplary embodiment, the top of the petri dish is no higher than the top of the top of upper flat portion 126 although this may vary. Likewise, the medium 150 and cells 152 are typically no higher than the top of portion 126.

Referring now to FIG. 15, chamber 1H is configured to use the packets or shelves 84A shown in FIG. 14. Chamber 1H is similar to chamber 1B shown in FIG. 7 except that chamber 1H shows a different shelving configuration. FIG. 15 illustrates that the lower packet or shelf 84A is removably positioned atop inner layer 68C of the bottom wall, similar to the lower packet 84 in FIG. 7. However, the middle packet or shelf 84A is seated atop a wire or other shelf 2 rather than on a tray 98 as in FIG. 7. The bottom walls 88 of each of the lower and middle shelves or packets 84A are atop a supporting surface or shelf whereby each packet 84A serves as a shelf on which the various items 40 are seated within interior chamber 4. The upper shelf 84A of chamber 1H is supported within interior chamber 4 in a different manner. More particularly, support ledges 154 are connected to and extend inwardly from the left and right walls defining interior chamber 4 in order to support the upper packet 84A respectively along its left and right side edges 94 and 96. FIG. 15 shows only one of support ledges 154, which extends from adjacent the back of interior chamber 4 to adjacent the front of interior chamber 4. Thus, packet 84A along the left and right edges 94 and 96 form respective lips which are seated on the support ledges 154. These lips or side edges of packet 84 easily slide along support ledges 154 to insert the packet or shelf 84A into chamber 4 or remove it therefrom via entrance opening 6 when door 5 is opened.

Figure 17:
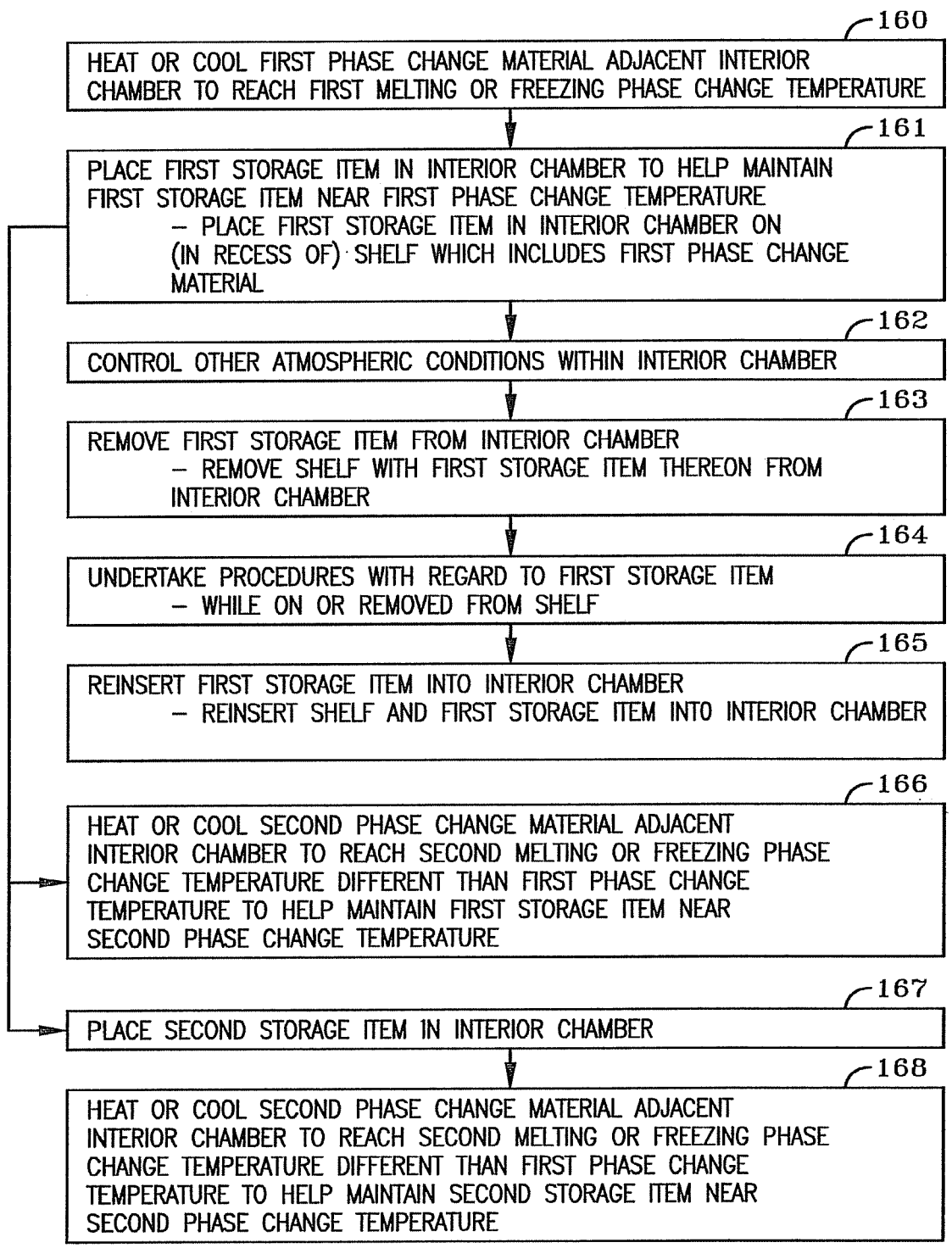
FIG. 17 is a flow chart illustrating various methods of the present invention.

Although each of the chambers described above vary somewhat from one another, all of them operate in essentially the same basic manner. Various processes of the present invention are illustrated in the flow chart of FIG. 17 at blocks 160-168 and will be referred to hereafter although not necessarily in the same order. Each insulated chamber is configured to control various atmospheric conditions within interior chamber 4 (block 162). For example, power source 25 provides the power for running the various electrical components of chamber 1, such as fan assembly 23, control units 17, 19, and 21, refrigeration assembly 28, heating unit 29 and the solenoid or other actuator of control valves 33 and 39. The user of chamber 1 manipulates the settings of temperature, humidity and $CO_2$ level within interior chamber 4 via control interface 15, which may include three or more buttons or controls as shown in FIG. 1 which correspond respectively to these three features. Sensors 27, 31 and 37 respectively sense or determine the temperature, humidity and $CO_2$ level within interior chamber 4 and produce respective signals which are sent respectively to temperature control unit 17, humidity control unit 19 and $CO_2$ control unit 21. Based on the signal from temperature sensor 27, temperature control unit 17 controls heating unit 29 to turn it off, turn it on and/or control the degree of heat produced thereby for providing heat within interior chamber 4 as well as heat to PCM material 58 radiated through the various inner layers 68 of skin 54. Temperature control unit 17 may also control refrigeration assembly 28 in response to the signal from temperature sensor 27 to control the degree of cooling provided thereby within interior chamber 4, such as by turning it off or turning it on. Based on the signal from humidity sensor 31, humidity control unit 19 controls the solenoid or other actuating mechanism for operating control valve 33 to increase or decrease the amount of moisture within interior chamber 4. Similarly, based on the signal from $CO_2$ sensor 37, $CO_2$ control unit 21 controls the solenoid or other actuating mechanism of control valve 39 in order to increase or decrease the amount of carbon dioxide entering interior chamber 4 in order to provide the appropriate level of $CO_2$ in accordance with the input settings. Fan assembly 23 may be operated to rotate the fan in order to gently blow the gas within interior chamber 4 to maintain a substantially uniform temperature, humidity and level of carbon dioxide throughout the chamber. Fan assembly 23 may be operated on a continuous basis or intermittently in a variety of predetermined patterns, which may be related to the opening and closing of door 5, especially to help recover the internal temperature and the $CO_2$ and humidity levels after the door has been opened and closed.

PCM 58 of the present invention helps to maintain interior chamber 4 at a substantially constant temperature due to the significant amount of latent heat which PCM 58 absorbs or releases during its phase change, namely melting or freezing. PCM 58 is especially helpful in maintaining that temperature if there is a loss of power to the heating element 29 or refrigeration assembly 28 for an extended period. More particularly, PCM 58 is configured to have a melting or freezing phase change temperature which is at or about a desired selected temperature of interior chamber 4. Thus, the storage item or items 40 may be placed in interior chamber 4 to help maintain the storage items near the phase change temperature of a given PCM 58 (block 161). Typically, the melting or freezing temperature of PCM 58 is within the range of about −40° C. (−40° F.) to about 150° C. (302° F.) or 160° C. (320° F.). However, the melting or freezing temperature of PCM 58 may be less or greater than this range.

In one embodiment, the melting temperature of PCM 58 is about 37° C. (98.6° F.) or in a range of 35-40° C. since this is one of the most commonly used temperatures for culturing bacteria and mammalian cells. One suitable phase change material which has a melting or freezing temperature of about 37° C. is available under the name "BioPCM Phase Change Material-37" from Phase Change Energy Solutions, Inc. of Asheboro, NC This product includes a phase change component and a fire suppression component. The phase change component is a derivative of fatty acids. The above noted business also produces PCMs which have respective melting or freezing temperatures anywhere within the range of about −40° C. to about 150° C. or 160° C. Similarly, phase change materials which are suitable for use as PCM 58 in the present invention are available from Entropy Solutions, Inc. of Minneapolis, MN Entropy Solutions, Inc. also produces a large variety of PCMs which have a respective melting temperature within the range of about −40° C. to about 150° C. or so. For example, one such PCM which melts or freezes at about 37° C. is available from Entropy Solutions, Inc. under the name "PureTemp 37." Likewise, Entropy Solutions, Inc. produces other PCMs, such as "PureTemp −40" having a melting point of about −40° C., "PureTemp −12" having a melting point of about −12° C., "PureTemp 4" having a melting point of about 4° C., "PureTemp 23" having a melting point of about 23° C., "PureTemp 30" having a melting temperature of about 30° C., "PureTemp 40" having a melting point of about 40° C. and "PureTemp 50" having a melting point of about 50° C. This company also produces a much wider variety of PCMs, for example PCMs (with analogous names) which have melting or freezing points respectively of about −14° C., about 7° C., about 15° C., about 18° C., about 27° C., about 30° C., about 43° C., about 48° C., about 53° C., about 55° C., about 56° C., about 61° C., about 68° C., about 103° C. and about 151° C. Entropy Solutions, Inc. is capable of producing a PCM of substantially any desired melting temperature. Entropy Solutions, Inc. indicates that the PCMs which they produce are from vegetable-based fats and oils. It is noted, however, that any suitable phase change material having the desired melting temperature may be used as PCM 58.

In some cases, it is desired to maintain the temperature of interior chamber 4 and item 40 at a temperature higher than room temperature (about 22 to 23° C. or 71 to 73° F.) or the ambient temperature, and thus PCM 58 is a solid at room temperature or at the ambient temperature. To take advantage of the phase change concept of such an embodiment of material 58, heating element 29 is operated in order to heat interior chamber 4 and the phase change material 58 until it melts at its melting phase change temperature (block 160). Most preferably, all of PCM 58 is melted so that PCM 58 is able to provide the greatest duration of substantially constant temperature during its phase change from the liquid state to the solid state while there may be no additional heat source available to maintain the interior temperature of interior chamber 4, such as during a power outage. In the heating scenario, each of the chambers positions the phase change material between the solid insulation and interior chamber 4, or positions the phase change material within interior chamber 4 itself so that insulation 56 of the container and the insulation of door 5A and/or the double paned window of door 5 substantially aids in preventing loss of heat from interior chamber 4.

In other cases, it is desired to maintain the temperature of interior chamber 4 and item 40 at a temperature lower than room temperature or the ambient temperature, and thus PCM 58 is a liquid at room temperature or at the ambient temperature. Thus, refrigeration assembly 28 is operated in order to cool interior chamber 4 and the phase change material 58 to its freezing point or phase change temperature so that it freezes or solidifies (block 160). Most preferably, all of PCM 58 is frozen or solidified so that PCM 58 is able to provide the greatest duration of substantially constant temperature during its phase change from the solid state to the liquid state while there may be no additional cooling or refrigeration source available to maintain the interior temperature of interior chamber 4, such as during a power outage. In the refrigeration scenario, the phase change material in the respective insulation chambers is positioned so that insulation 56 of the container and the insulation of door 5A and/or the double paned window of door 5 substantially aids in preventing the transfer of external heat into interior chamber 4.

Although PCM 58 is well suited to help maintain the temperature during a power outage, it also helps in a variety of other situations. For instance, PCM 58 helps maintain and/or expedite recovery of the desired temperature within interior chamber 4 during and after door 5 is opened (FIG. 1) such as when item or items 40 are inserted and/or removed from interior chamber 4 (Arrows A in FIGS. 2, 5, 7-11, 13). Further, PCM 58 helps maintain or expedite recovery of the desired temperature when the temperature in chamber 4 is otherwise changed (increased or decreased) due to such factors as electrical power fluctuations, gas injections such as injection of carbon dioxide via $CO_2$ control unit 21, liquid injections such as injection of water via humidity control unit 19, exothermic or endothermic reactions occurring within item or items 40, and electronic devices which are part of an item 40. Such an electronic device might be, for example, lighting equipment such as might be used to simulate sunlight for growing plants, such that the light would produce heat when turned on within chamber 4. Another type of such an electronic device is a water pump for pumping water through an aqua tank, such as used for growing algae. Other examples of such an electronic device are a shaker for agitating a solution to facilitate growth, or a cell roller for rolling a bottle back and forth. Any of these electronic devices or others would during operation produce heat which would likewise tend to heat chamber 4 and any item therein. In addition, turning such electronic devices off while in chamber 4 would reduce the amount of heat energy that the electronic device produced within chamber 4 and thus alter the temperature in chamber 4. Likewise, altering the operation of such electronic devices in particular ways may also change the amount of heat that the device produces within chamber 4 at a given time. PCM 58 thus helps to maintain and/or facilitate recovery of the desired chamber 4 temperature in all of these scenarios or any other situation which would affect the internal temperature of chamber 4.

PCM 58 enhances the ability to maintain the stability of the temperature within chamber 4 as well as the uniformity of the temperature throughout chamber 4. The use of PCM 58 also enhances humidity uniformity in chamber 4 in combination with the humidity controls of the insulated chambers of the present invention, such that a stable dew point can be created in chamber 4, and the formation of condensation on items within chamber 4 or the walls defining chamber 4 can be minimized or eliminated. While the usefulness of PCM 58 has been described primarily as being related to its phase change characteristics, it is worth noting that PCM 58 also acts as an effective thermal mass and/or a thermal insulator.

It is also noted that other than PCM 58 and possibly the liquid medium 105, the other components of the various insulated chambers of the present invention are not considered to be PCMs, but rather remain in a single state, typically solid, throughout the entire range of the operational parameters of the given insulated chamber. Thus, among the components that remain in a solid state over the entire operational parameter of the insulated chambers of the present invention are the skins of the container and door, the control assembly, the various layers of insulation 70 and the like, the various control units, sensors and control valves, the heating and cooling devices (other than the liquid refrigerant within the cooling device), glass panes of the door where used, the seals used between the panes and between the door and the container, the wire or other similar shelves, the outer skin of the PCM packets, the fan assembly, the solid matrix when used, and any other components which would obviously remain in a solid state during the normal operational parameters of the insulated chamber.

Although the various insulated chambers described herein are similar, the certain aspects of the configurations may be more suited to certain purposes. For example, the upper and middle packets 84 in chamber 1B (FIG. 7) are positioned below and adjacent the respective shelf 2 and item 40 thereon, which is better suited for when the desired temperature of chamber 4 and item 40 is above the ambient temperature. On the other hand, the upper packet 84 in chamber 1C (FIG. 8) is positioned above and adjacent the upper shelf 2 and upper item 40 thereon, which is better suited for when the desired temperature of chamber 4 and item 40 is below the ambient temperature. Generally, the PCM is distributed strategically to enhance natural convection, and thus more PCM is located toward the bottom of chamber 4 when the desired chamber 4 temperature and PCM melting temperature is above the ambient temperature, whereas more PCM is located toward the top of chamber 4 when the desired chamber 4 temperature and PCM melting temperature is below the ambient temperature. In addition, more PCM is typically positioned adjacent the door opening to offset the heat loss path created in this area. It is further noted that various of the thermally conductive materials used in the present invention enhance thermal conduction between the PCM and interior chamber 4 and between the PCM and components within chamber 4 including item 40. In particular, layers 86 and 88 of packet 84 enhance such thermal conduction, as do inner layer 62 of skin 54 (FIGS. 2, 3) and inner layer 80 of skin 74 of door 5A (FIG. 5).

Figure 16:
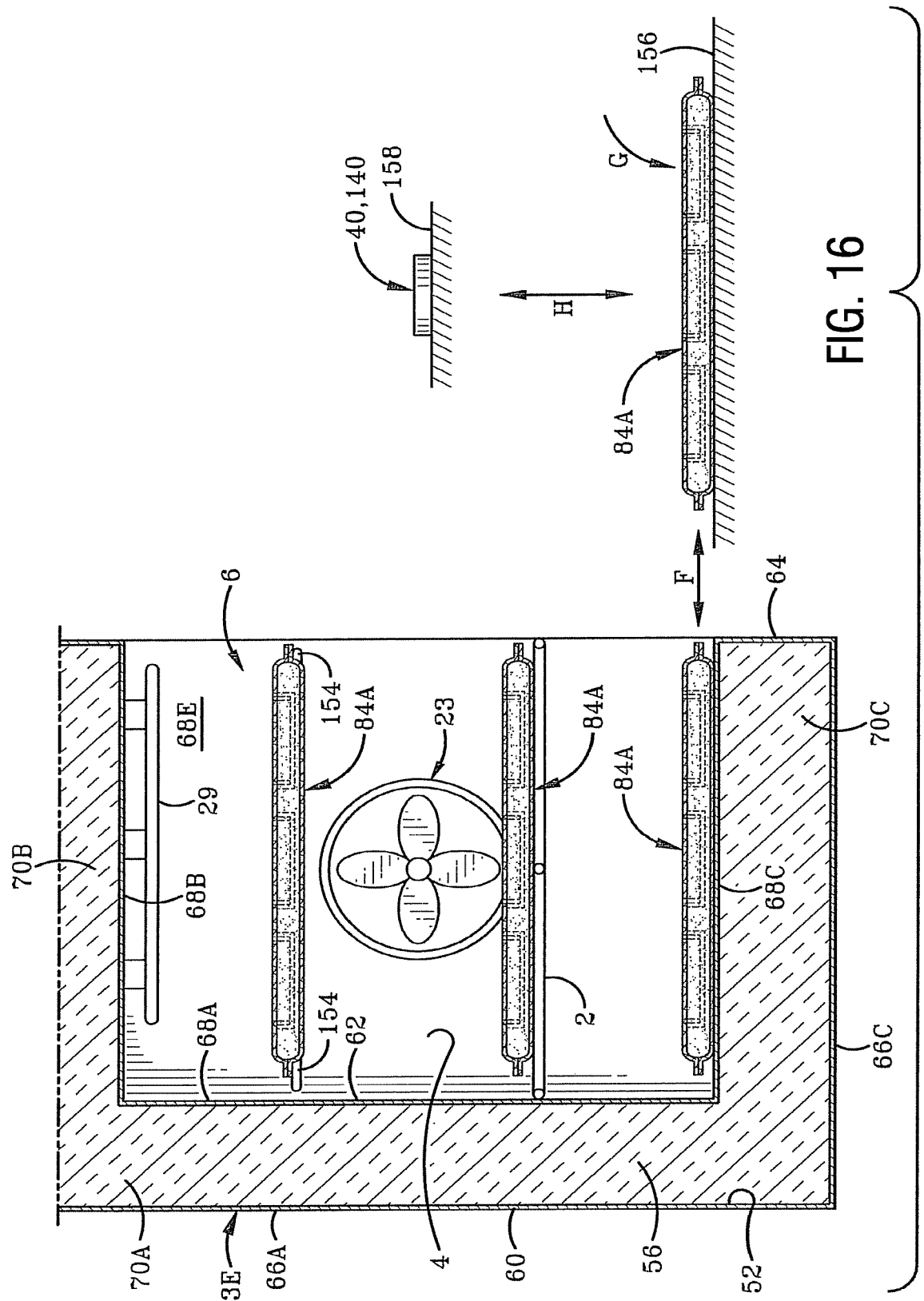
FIG. 16 is a sectional view similar to FIG. 15 with the door removed and portions cut away to illustrate the use of the PCM packets or shelves inside and outside of the chamber.

FIG. 16 illustrates an additional advantage of using packets or shelves 84A. More particularly, each shelf 84A is removable from and insertable into interior chamber 4 with items 40 thereon within recesses 128, as indicated at arrow F (block 161). Thus, a given packet 84A may be removed from interior chamber 4 and placed at a position outside the interior chamber 4 such as on a support surface 156 while the storage items 40, shown here as petri dishes 140, and the contents thereof, remain seated on the shelf within recesses 128 (block 163). While the storage items 40 and/or shelves 84A are removed from interior chamber 4, various procedures may be undertaken with regard to the storage items, either while the storage items are on or removed from the given shelf 84A or a similar shelf (block 164). Support surface 156 may, for example, be in the form of a table or a counter which is part of a fume hood whereby fumes from the petri dishes or other items under the hood may be exhausted. During the culturing of cells 152, it is necessary for the cells to be fed a suitable food, as indicated at arrow G. Thus, a worker may feed the cells 152 on medium 150 while the petri dish is seated within recesses 128 on packet 84A while the packet is on support surface 156 within a fume hood or the like. When the petri dishes are placed within recesses such as recesses 128, or remain seated atop a PCM packet like packet 84 in FIG. 6, the PCM of the corresponding packet helps to maintain the desired temperature of the item 40, including the medium 150 and cells 152 while they are outside the interior chamber 4 of insulated chamber 1H or the like. In addition, FIG. 16 illustrates that a given petri dish or other storage item 40 may be removed from the shelf or packet 84A when both are outside interior chamber 4 in order that the storage item 40 may be manipulated for other purposes. For example, storage item 40 may be removed from the packet (arrow H) and seated on another support surface 158. Support surface 158 also represents, for example, a scale on which item 40 may be weighed, or a microscope so that cells 152 or other components of item 40 may be viewed under the microscope. After a given item 40 has been manipulated on surface 158 or by any given tool as desired, it may be returned to the recess of packet 84 (arrow H) and other items 40 may similarly be removed and reinserted on packet 84. Once all procedures involving storage items 40 have been performed outside the insulated chamber, packet 84 with the various items 40 may be reinserted into interior chamber 4 (block 165).

Each of the chambers of the present invention may also be configured with two or more PCMs each of which has a different melting or freezing point. Thus, for example, one or more of layers 72A-E of chamber 1 (FIGS. 2-4) or layers 72A-F of chamber 1A (FIG. 5) may be formed of one PCM having a first melting or freezing phase change temperature while one or more of the other of said layers 72 may be formed of a PCM having a second melting or freezing phase change temperature which is different than the first melting or freezing temperature. Similarly, the layer 72G within one of packets 84 of chambers 1B or 1C (FIG. 7-8) may be formed of a PCM having the first melting or freezing temperature while another one of the layers 72G of the corresponding chamber 1B or 1C is formed of a PCM having the second melting or freezing temperature. Likewise, the layers 72A of chambers 1D or 1E (FIGS. 9-10) may have the first melting or freezing temperature while the respective layer 72B has the second melting or freezing temperature. Moreover, any one of the above noted PCM layers 72 may be formed of two or more different PCMs each having different melting temperatures. Whether these two or more PCMs are in separate layers or intermixed, the chamber thus provides the corresponding PCM for the respective first, second or third selected internal temperature of the interior chamber. In addition, the encapsulated pellets 104 of chambers 1F and 1G (FIGS. 11 and 13) may include two or more batches of pellets 104 such that the PCM 58 within one batch has a melting or freezing phase change temperature which is different than that of the other batch or batches. Configuring the chambers to have PCMs with differing melting or freezing temperatures may be useful, for example, in the pharmaceutical industry. In particular, drug manufacturers run stability tests on various medicines respectively at 30° C. and 40° C. (104° F.). Thus, the chambers of the present invention may be configured with one PCM having a melting point of about 30° C. and another PCM having a melting point of about 40° C. to facilitate maintaining the temperature of interior chamber 4 at the corresponding temperature as desired by the user. The melting or freezing phase change temperatures of the two PCMs in the above example are both, for example, above 0° C. and above the typical ambient temperature or typical room temperature of about 22° C. or 23° C. However, two or more PCMs used with a given insulated chamber of the present invention may also be configured to have melting or freezing phase change temperatures which are both below 0° C., the ambient temperature or the room temperature noted above, or may also be configured such that the phase change temperature of one of the PCMs is above one of these reference temperatures and the other is below the corresponding reference temperature.

Thus, where the chamber utilizes two phase change materials each having different melting or freezing phase change temperatures, the chamber may be operated to either heat or cool the first phase change material with one of the heating or cooling devices carried by the chamber to melt or freeze the first phase change material at its melting or freezing temperature while also heating or cooling the interior chamber to that temperature and incubating, storing or maintaining a given item within the interior chamber at about this first melting or freezing temperature. Subsequently, the chamber may be similarly operated to heat or cool the second phase change material and the interior chamber at a second melting or freezing phase change temperature of the second phase change material such that it melts or freezes. Then, either the item that was incubated, stored or maintained at the first temperature may also be incubated, stored or maintained at the second temperature (block 166), or it may be removed and another item may be inserted into interior chamber 4 (block 167) and incubated, stored or maintained at or near the second temperature (block 168). It is noted that the processes illustrated in FIG. 17 do not necessarily occur in the order shown nor are the processes necessarily separate as might be suggested by the arrows.

One aspect of the present invention relates to a novel and non-obvious method and system employing a new H2O2 cycle to decontaminate cell culture incubators. One advantageous feature of the current invention comprises a H2O2 cleaning cycle that consolidates two steps in the prior art into one step thereby advantageously shortening the H2O2 cleaning cycle. Another advantageous feature of the current invention comprises a H2O2 cleaning cycle with a shortened sterilization step, relative to the sterilization step of the prior art cleaning cycle. In addition to reducing the number of steps, the present invention employs a 'dry' H2O2 cycle, distinguishing it from the prior art 'wet' cycles.

Figure 19:
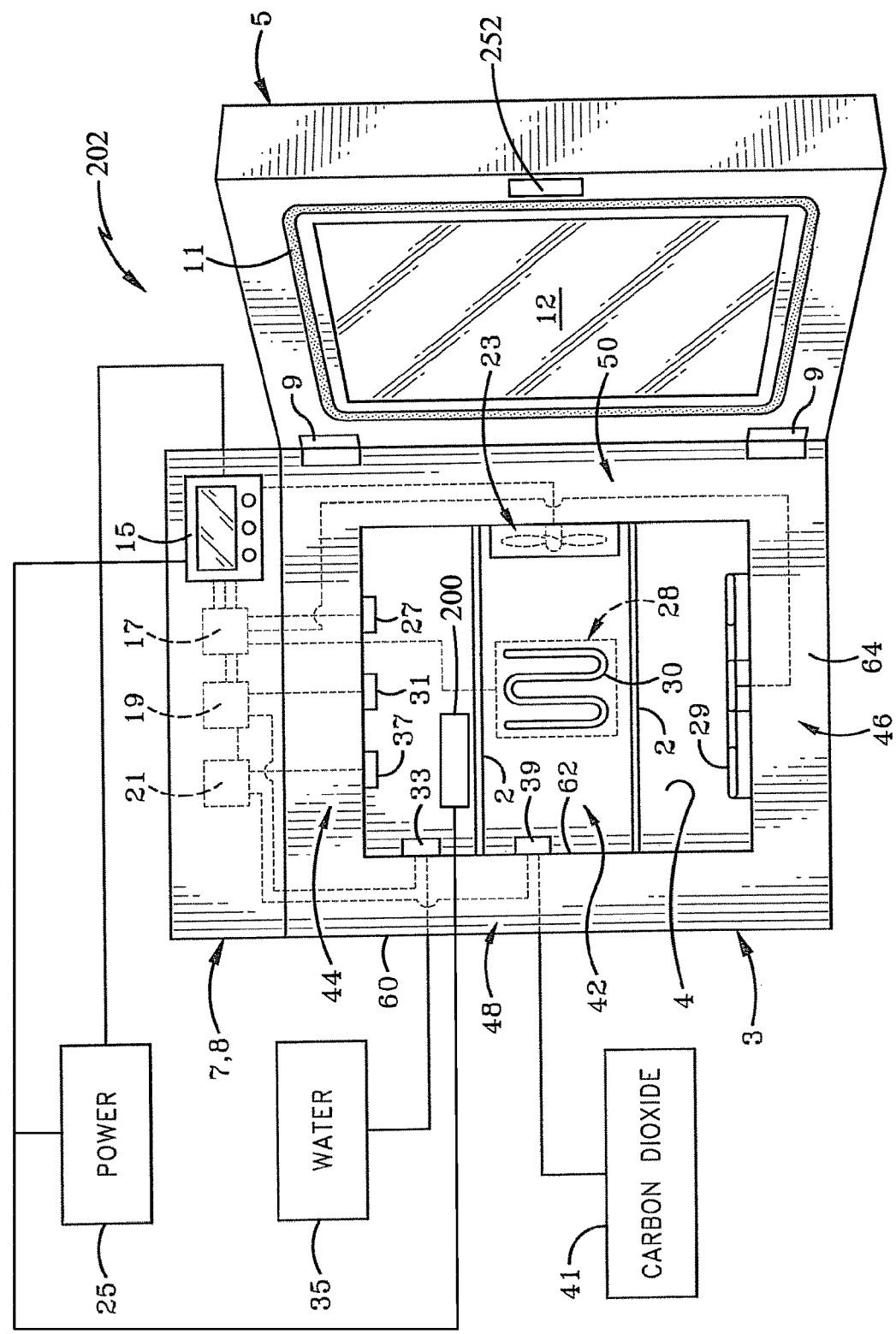
FIG. 19 is a front elevational view of an embodiment of a system for vaporized hydrogen peroxide cleaning of an incubation chamber.

FIG. 19 is a front elevational view of an embodiment of a system 202 for vaporized hydrogen peroxide cleaning of an incubation chamber. The system 202 includes the container 3 discussed in the above embodiments, and a module 200 positioned on a shelf 2 of the container 3 for vaporized hydrogen peroxide cleaning of the incubation chamber 4 of the container 3. In one embodiment, the material 40 has been removed from the shelves 2 and replaced by the module 200. As depicted in the embodiment of FIG. 19, the module 200 is communicatively coupled to the power source 25 and the control interface 15, to perform various steps of the method for vaporized hydrogen peroxide cleaning of the incubation chamber 4 of the container 3, as discussed in greater detail below.

In some embodiments, the container 3 of the system 202 does not include any PCM material. In other embodiments, the container 3 of the system 202 includes PCM material, including any one of the arrangements of PCM material discussed above in the above embodiments of FIGS. 1-17. In one example embodiment, the container 3 of the system 202 includes an arrangement of PCM material that is similar to the embodiment of FIG. 5, the embodiment of FIG. 9 or some combination thereof. In another example embodiment, the container 3 of the system 202 includes a combination of the embodiments of FIG. 5 and FIG. 9, specifically a heating element 29 inside the chamber 4 (FIG. 5) and a heating element 29A between the insulation 56 and the PCM 72 (FIG. 9). In this example embodiment, the heating element 29 inside the chamber 4 is provided to quickly achieve elevated incubator air temperature within the chamber 4 and the heating element 29A is provided to melt the PCM material 72 and is used for steady state control during the H2O2 cleaning process.

Although the system 202 depicts the module 200 positioned within the container 3, the module 200 and method for vaporized hydrogen peroxide cleaning of an incubation chamber is not limited to use with any particular incubator, such as the container 3. In one embodiment, the specific temperature levels, the humidity levels and the time periods of each step of the method discussed herein will vary, depending on one or more parameters of the incubator, such as the size of the interior chamber and concentration of H2O2 solution. Additionally, in other embodiments, the components of the system 202 can vary, depending on one or more parameters of the incubator. In an example embodiment, more than one temperature sensor 27 and/or more than one humidity sensor 31 and/or more than one module 200 may be positioned within the chamber 4, depending on the size of the interior chamber 4. The numerical parameters of the method discussed herein are merely one example embodiment of the method for vaporized hydrogen peroxide cleaning of the interior chamber 4 of the container 3 using the module 200 and thus the method using the module 200 with other incubators with different sized chambers will have different temperature levels, humidity levels and time periods than those discussed herein. In one example embodiment, the container 3 is sized such that the dimensions of the interior chamber 4 are 31.3" width (from left side to right side), 9.5" depth (from back to front) and 26" height, with an approximate volume of 5 ft$^3$. In another example embodiment, the container 3 is sized such that the dimensions of the interior chamber 4 are 32" width, 27" depth and 52.7" height, with an approximate volume of 25 ft$^3$. In another example embodiment, the container 3 is sized such that the dimensions of the interior chamber 4 are 32" width, 27" depth and 65.7" height, with an approximate volume of 33 ft$^3$. In another example embodiment, the container 3 is sized such that the dimensions of the interior chamber 4 are 23" width, 25.8" depth and 29.8" height, with an approximate volume of 10 ft$^3$. In still other embodiments, the container 3 is sized such that the dimensions of the interior chamber 4 include a width in a range of 23-32", a depth in a range from 9-27" and a height in a range from 26-66". However, the embodiments of the container 3 are not limited to interior chambers 4 with these specific numerical dimensions or dimensional ranges.

Figure 20A:
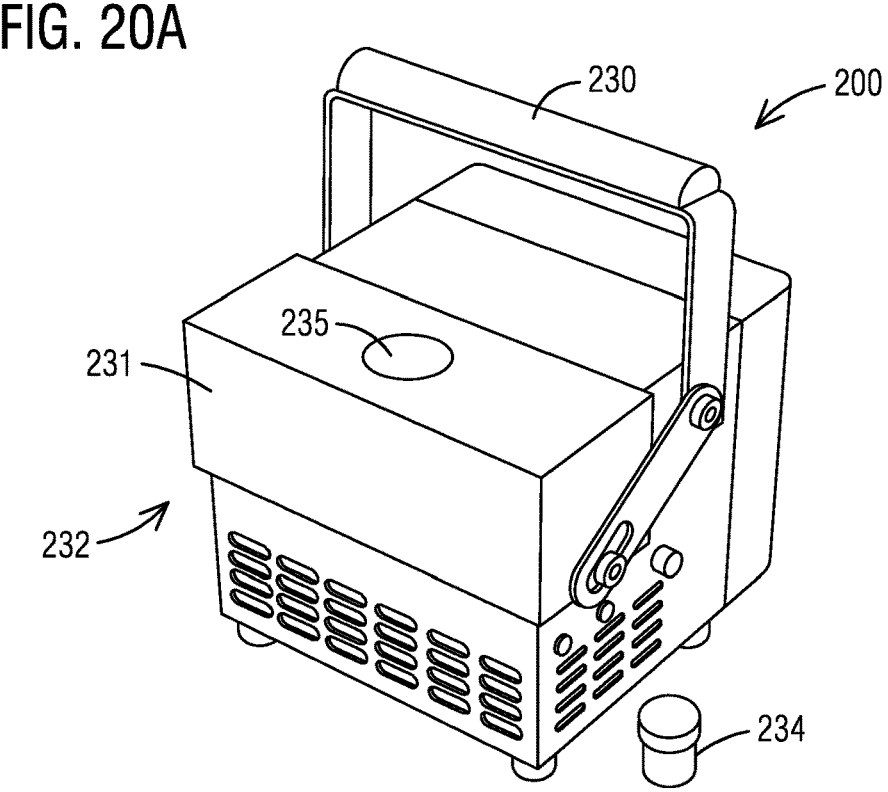
FIGS. 20A-20B are front perspective views of one embodiment of a module for vaporized hydrogen peroxide cleaning of an incubation chamber.
Figure 20B:
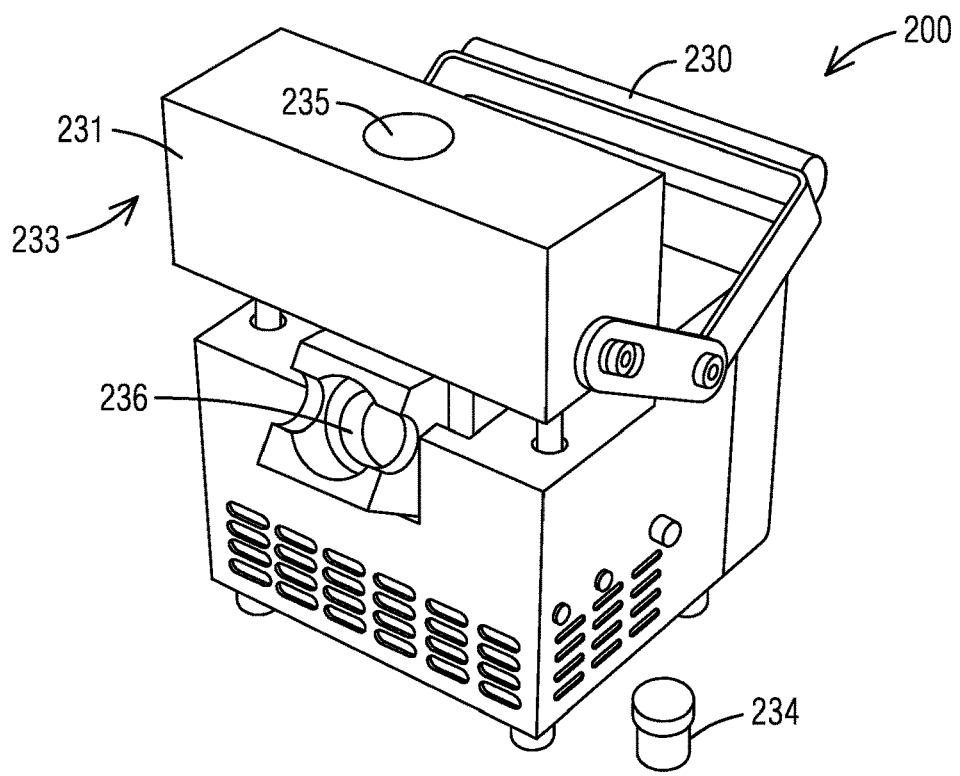

FIGS. 20A-20B are front perspective views of one embodiment of the module 200 for vaporized hydrogen peroxide cleaning of the incubation chamber 4. FIG. 20A shows a handle 230 of the module 200 in a closed position and a front end 231 of the module 200 in a closed position 232, based on the handle 230 in the closed position. FIG. 20B shows the handle 230 moved from the closed position of FIG. 20A to an open position, which in turn causes the front end 231 to move upward to an open position 233 and reveal a receptacle 236. In an embodiment, the receptacle 236 is sized to receive a cartridge 234 of H202, such as 35% H202 for vaporized injection in the chamber 4. In some embodiments, the H202 concentration of the cartridge 234 is in a range of 30-40%. In other embodiments, the H202 concentration of the cartridge 234 is in a range from 15-65% and in another embodiment, the H202 concentration of the cartridge 234 is in a range from 25-59%. In an embodiment, the cartridge 234 is disposable after each cleaning cycle. The module includes an injection item for injecting H202. In some embodiments, the injection item is a piezo ultrasonic device 235 that is positioned over the receptacle 236. After the cartridge 234 is inserted in the receptacle 236 and the piezo ultrasonic device 235 receives a signal to initiate the injection cycle, the piezo ultrasonic device 235 commences to inject the vaporized H202 from the cartridge 234 and into the incubator chamber where the module 200 is positioned. The injection item is not limited to the module 200 or the piezo ultrasonic device 235 and includes any injection item known to one of ordinary skill in the art that is capable of injecting vaporized H202.

Figure 21A:
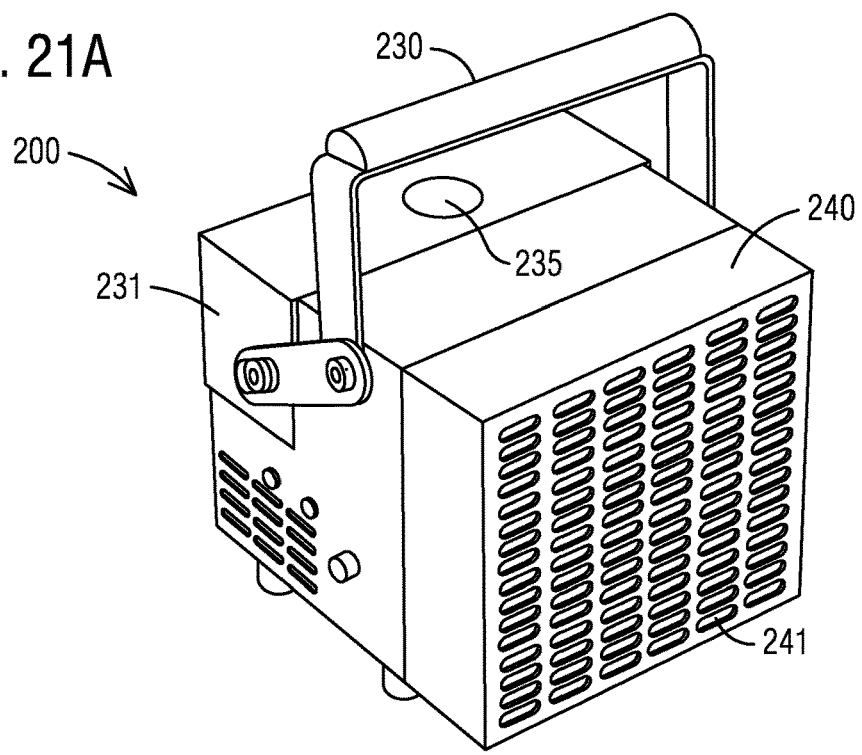
FIGS. 21A-21B are rear perspective views of the embodiment of the module of FIGS. 20A-20B.
Figure 21B:
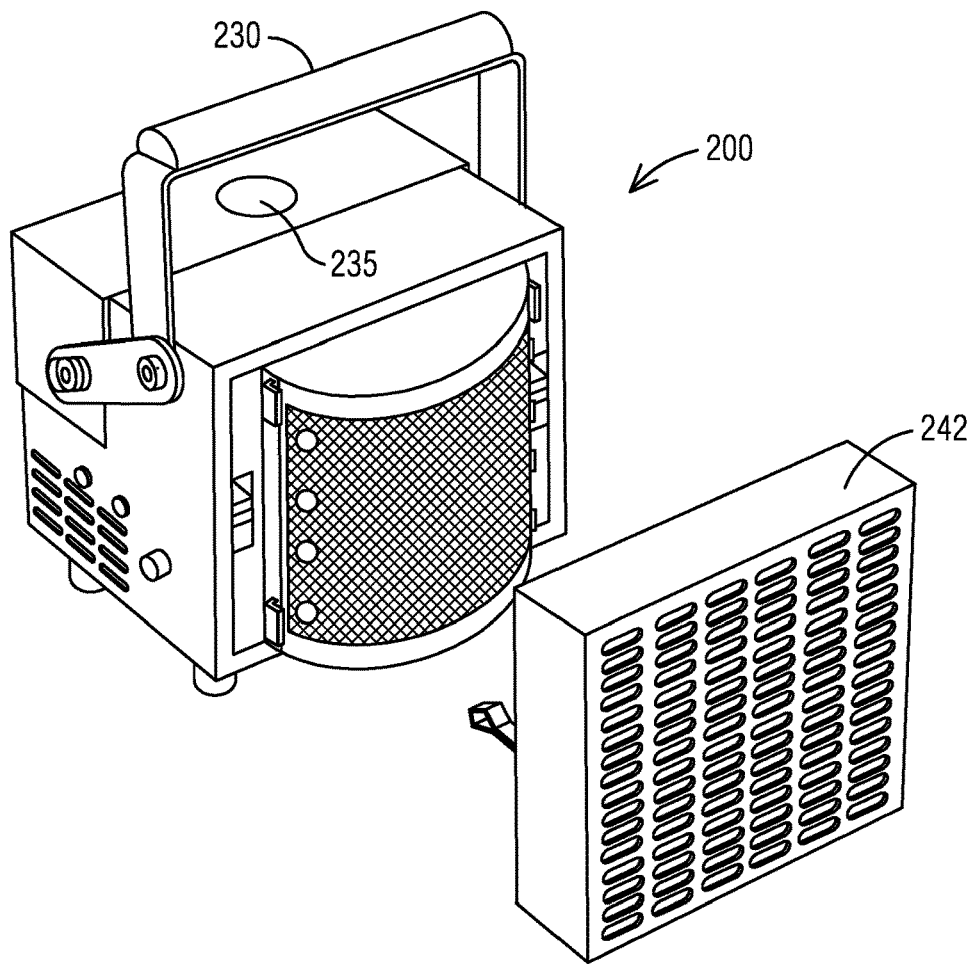

FIGS. 21A-21B are rear perspective views of the embodiment of the module 200 of FIGS. 20A-20B. The end 240 of the module 200 includes a grating or vent 241. A removable piece 242 of the end 240 can be detached to expose a catalyst 244 mounted within the module 200, such as a silver catalyst, for example. In one embodiment, during one stage of the cleaning cycle, air containing H202 within the interior chamber 4 is passed through the silver catalyst 244 and through the vent 240 to reduce the level of H202 in the air within the interior chamber 4. Upon passing through the silver catalyst 244, the H202 in the air is converted to vaporized H20 and O2.

Figure 22A:
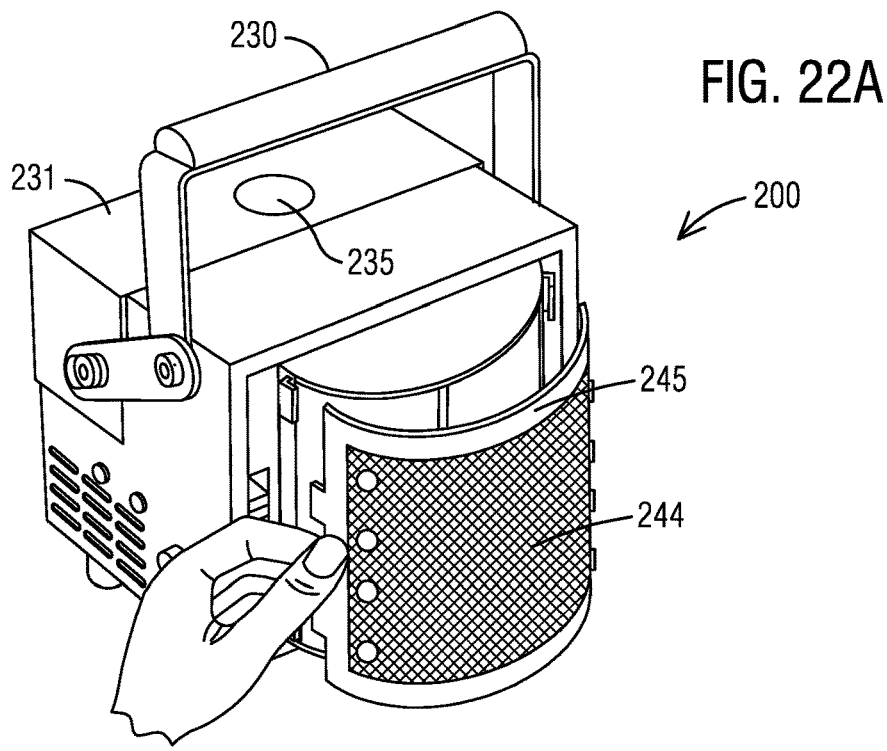
FIGS. 22A-22B are perspective views of one embodiment of a catalyst and fan positioned within the module of FIGS. 21A-21B.
Figure 22B:
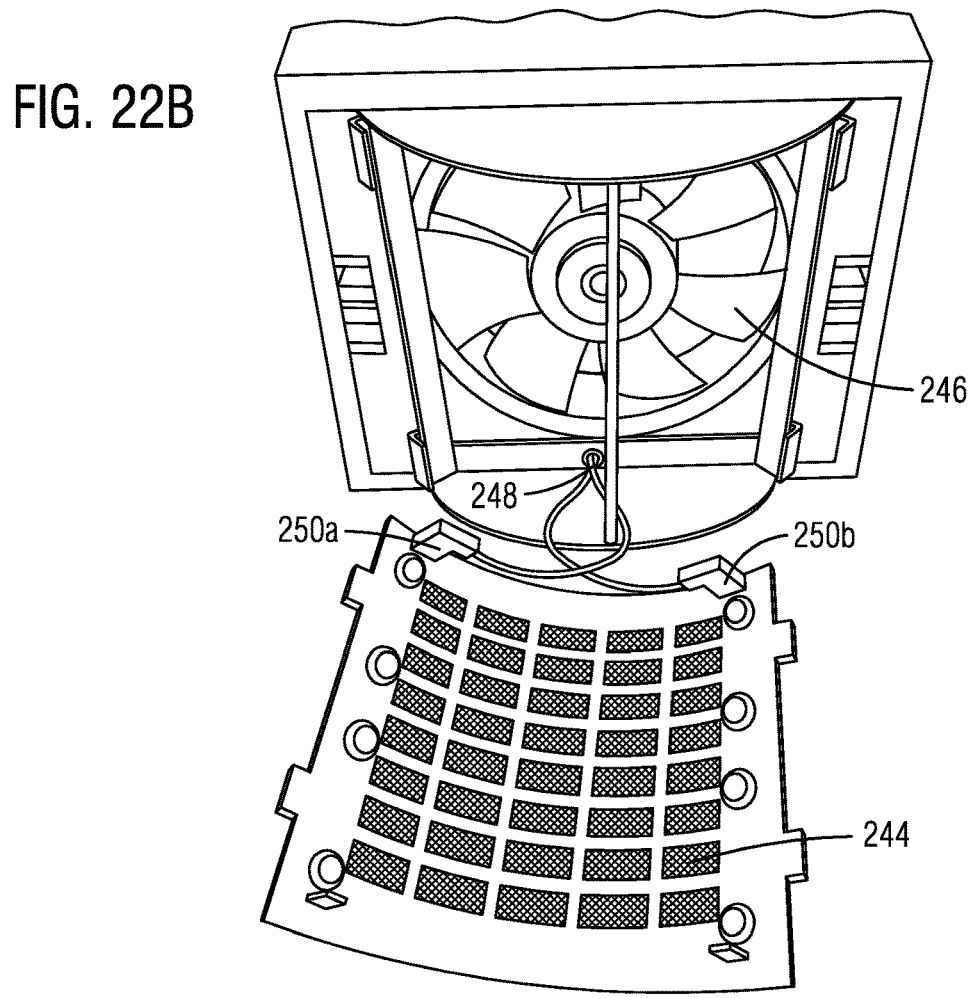

FIGS. 22A-22B are perspective views of one embodiment of the catalyst 244 and fan 246 positioned within the module 200 of FIGS. 21A-21B. In one embodiment, the silver catalyst 244 is mounted on a frame 245 and securely fixed within the module 200 between a fan 246 and the vent 241. In this embodiment, during a phase of the cleaning cycle discussed herein, in order to reduce a level of H202 within the interior chamber 4, air is drawn into the module 200 by the fan 246 and through the silver catalyst 244 to reduce a level of H202 in the air before the air is exhausted through the vent 240 back into the interior chamber 4. As shown in FIGS. 22A-22B, the module 200 includes wiring 248 (positive and ground cables) that are respectively coupled at respective connections 250a, 250b in order to apply a voltage across the catalyst 244 and measure one or more electrical properties of the silver catalyst 244, such as electrical resistance, for example. In this example embodiment, the measurement of the one or more electrical properties is used to indicate whether or not the silver catalyst 244 has remaining useful life and thus can still effectively reduce the level of H202 in air passed through the catalyst 244 by the fan 246.

FIG. 23 is a partial block diagram of the embodiment of the system 202 of FIG. 19. Indeed, the block diagram of FIG. 23 does not depict all components of the system 202 involved in the H202 cleaning cycle of the interior chamber 4 of the container 3, as other drawings (e.g. FIG. 1) depict other such components and will be discussed herein.

FIG. 24 depicts a flowchart of a method 400 for operating the system 202 during an H202 cleaning cycle. Although steps are depicted in FIG. 24 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. In step 401, prior to initiating the H202 cleaning cycle, contents (e.g. the material 40, see FIG. 1) is removed from the shelves 2 of the container 3. In step 402, a full H202 cartridge 234 is loaded into the module receptacle 236. In step 403, the module 200 is then positioned on a shelf 2 in the interior chamber 4 of the container 3, as shown in FIG. 19. In step 405, the module 200 is then connected to the power source 25 and control interface 15 of the container 3, as shown in FIGS. 19 and 23.

In step 407, in one embodiment, once the control interface 15 detects the module 200, the control interface 15 is configured to determine whether the catalyst 244 is present and has remaining useful life. In an embodiment, each catalyst 244 has 100 or more useful cycles. As shown in FIG. 23, in this embodiment, the control interface 15 transmits a signal to the power source 25 to apply a voltage with the wiring 248 across the connections 250a, 250b and measures a resistance across the catalyst 244. In one embodiment, the control interface 15 is communicatively coupled to an ohmmeter 243 that measures the resistance across the catalyst 244 and receives a signal of the measured resistance from the ohmmeter 243. Based on the measured resistance of the catalyst 244, the control interface 15 determines whether the catalyst 244 has remaining useful life (e.g. is in good working condition) and thus can effectively convert the H202 content in air passed through the catalyst 244 to water (H20) and oxygen gas (O2). In some embodiments, the control interface 15 determines that the catalyst 244 has remaining useful life if the measured resistance is less than a threshold resistance. In an example embodiment, the threshold resistance is 300 ohms. However, the threshold resistance is not limited to this numerical value and may vary depending on one or more characteristics of the catalyst. In an example embodiment, a low voltage DC current source is used to measure the catalyst resistance. In addition to verifying useful life of the catalyst 244, step 407 is employed to verify the presence of the catalyst 244. In some embodiments, a sensor is provided to sense the presence of the catalyst 244 and transmits a signal to the control interface 15 based on whether the catalyst 244 is present. In this embodiment, the control interface 15 determines that the catalyst 244 is present, based on the received signal from the sensor.

In step 409, if the control interface 15 determines that the catalyst 244 does have remaining useful life and is present, the control interface 15 prompts the user to initiate the H202 cleaning cycle using one or more buttons (see FIG. 19) on the control interface 15. In other embodiments, the control interface 15 automatically initiates the H202 cleaning process after steps 405 and 407. If the control interface 15 determines that the catalyst 244 does not have remaining useful life or is not present, the control interface 15 outputs this determination and will not prompt the user to initiate the H202 cleaning cycle or initiate the H202 cleaning cycle. In one embodiment, the control interface 15 is configured to prevent an initiation of the H202 cleaning cycle until the control interface 15 has determined that the catalyst 244 has remaining useful life and is present.

Additionally, in step 411, in an example embodiment, at the same time that the user presses the button on the control interface 15 to initiate the H202 cleaning cycle, the control interface 15 transmits a signal to a door lock 252 (FIG. 19, FIG. 23) to lock the door 5 of the container 3 during the H202 cycle. However, step 411 is not limited to this arrangement. In other embodiments, the door lock 252 is a manual mechanical door lock that is manually engaged by the user in step 411 after the user initiates the H202 cleaning cycle in step 409. In still other embodiments, no door lock 252 is used and thus step 411 is not performed. In this example embodiment, the door lock 252 remains engaged and thus the door 5 remains locked until completion of the H202 cleaning cycle (e.g. until the level of H202 in the interior chamber 4 reaches a safe level, as discussed below), at which time the control interface 15 transmits a signal to the lock 252 to disengage the lock 252 so that the door 5 can be opened. However, the door lock 252 and step 411 are merely optional features and need not be included in the system 202 or method 400. In other embodiments, the control interface 15 performs other safety measures after the H202 cleaning cycle is initiated, including flashing a colored warning sign on the interface 15 to caution the user not to open the door 5 of the container 3 during the H202 cycle. In another embodiment, if the control interface 15 detects that the door 5 is opened during the H202 cycle, the control interface 15 initiates an alarm. In another embodiment, the control interface 15 features an "abort" option, which the user can press which causes the control interface 15 to jump to a final step of the H202 cleaning cycle (e.g. step 507 as discussed below).

Figure 25:
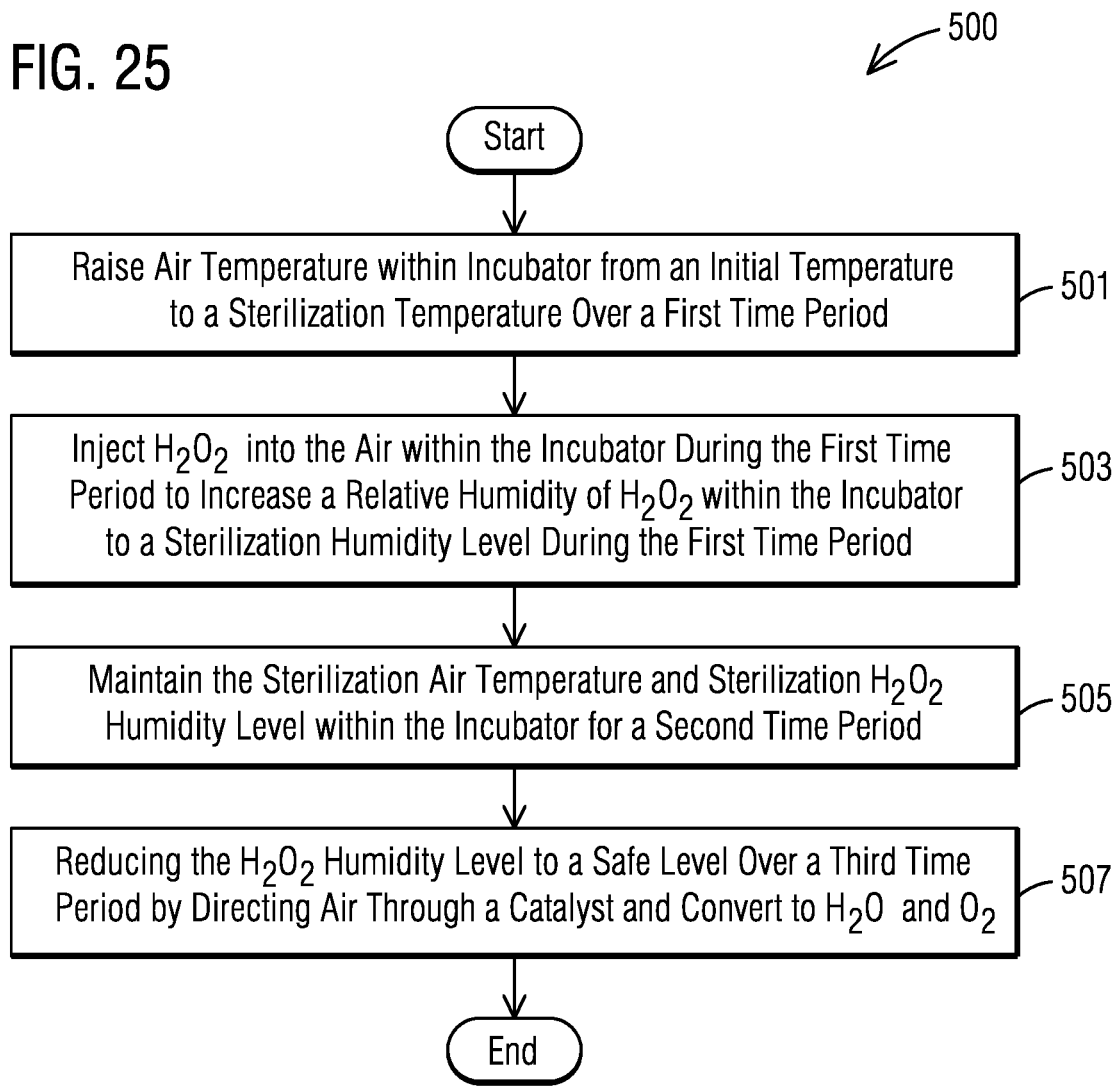
FIG. 25 is a flowchart depicting one embodiment of a method for vaporized hydrogen peroxide cleaning of an incubation chamber.

FIG. 25 depicts a flowchart of a method 500 for performing the H202 cleaning cycle of the interior chamber 4 with the module 200. Although steps are depicted in FIG. 25 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. In step 501, after the user presses the button on the control interface 15 to initiate the H202 cleaning cycle (step 409), the control interface 15 transmits a signal to the temperature control unit 17 (see FIG. 19) to raise the temperature within the interior chamber 4 to a sterilization temperature (e.g. 37C). The temperature control unit 17 activates the heating device 29 (FIG. 19) until the measured temperature by temperature sensor 27 is at the sterilization temperature. In some embodiments, the temperature control unit 17 is incorporated into the control interface 15 and thus the control interface 15 transmits a signal to the heating device 29 to raise the temperature within the interior chamber 4 until the measured temperature reaches the sterilization temperature.

Additionally, at the same time that the control interface 15 signals the temperature control unit 17, in step 503 the control interface 15 transmits a signal (see FIG. 23) to an injection item (e.g. the piezo ultrasonic device 235) within the module 200 to initiate injection of vaporized H202 (e.g. 35%) from the cartridge 234 into the interior chamber 4. In a first embodiment of injecting the H202, a humidity sensor 31*a* (see FIG. 19 and FIG. 23) is positioned within the interior chamber 4 to measure a combined humidity of H202 and H20 in the air. After the piezo ultrasonic device 235 receives the signal from the control interface 15, the piezo ultrasonic device 235 commences to inject vaporized H202 into the air within the chamber 4 which increases the combined humidity of H202 and H20. The humidity sensor 31*a* continuously measures the combined humidity of H202 and H20 within the chamber 4 and transmits a signal to the control interface 15 to communicate the measured combined humidity. When the combined humidity within the chamber 4 reaches a sterilizing level (e.g. 90%), the control interface 15 sends a signal to the piezo ultrasonic device 235 to cease the injection of H202 within the chamber 4.

In a second embodiment of injecting H202, a predetermined humidity injection profile is stored in a memory of the control interface 15. In some embodiments, the predetermined humidity injection profile includes a specified percentage 'on-time' of the injection system (e.g. injection rate) that varies over time. The percentage 'on-time' of the injection system represents a percentage or ratio of the time period that the injection item (e.g. piezo ultrasonic device 235) is activated. In an example embodiment, the injection profile approximates the injection profile of the first embodiment of injecting H202 discussed above. This second embodiment of injecting H202 is advantageously less expensive than other methods of injecting H202. In some embodiments, the percentage 'on-time' of the injection item (e.g. piezo ultrasonic device 235) is related to the temperature in the chamber 4 over time. In an example embodiment, the percentage 'on-time' of the injection item is related to the temperature in the chamber 4 as:

$$\% = 1.06 \times T - 22 \qquad (1)$$

where % is the percentage 'on-time' of the injection item to maintain 90% relative humidity in the chamber 4 and T is the temperature of the air in the chamber 4 (in units of Celsius, C). In one embodiment, the memory of the control interface 15 includes equation 1 and the memory of the control interface 15 computes the percentage 'on-time' of the injection item based on an input temperature T of the chamber 4 from the temperature sensor 27. During the first time period 212 (see below), the control interface 15 signals the injection item (e.g. piezo ultrasonic device 235) in accordance with this computed percentage 'on-time', so that the injection item remains on for the computed percentage of the first time period 212. In a third embodiment of injecting H202, a pair of humidity sensors 31a, 31b are provided within the chamber 4, where the humidity sensors 31a, 31b are similar with the exception that the humidity sensor 31b includes a filter to remove H202 from the measured air and thus the humidity sensor 31b only measures the relative humidity of H20 in the air. In an example embodiment, the filter is a catalyst 249 that functions in a similar manner as the catalyst 244 (e.g. removes H202 from air passed through the catalyst). This third embodiment of injecting H202 is similar to the first embodiment of injecting H202, with the exception that the additional humidity sensor 31b advantageously provides additional data (e.g. level 222 in FIG. 26 discussed below) including the relative humidity of only the H20 in the air. In an embodiment, a relative humidity of only the H202 in the air can be determined by subtracting the level of sensor 31b from the level of sensor 31a. In an example embodiment, the relative humidity of only the H202 in the air is increased to a range from 20-30%. In some embodiments, the relative humidity of only the H202 during the second time period 216 (e.g. sterilization) is a dependent variable on the combined humidity 224 (e.g. 90%) during sterilization.

Figure 26:
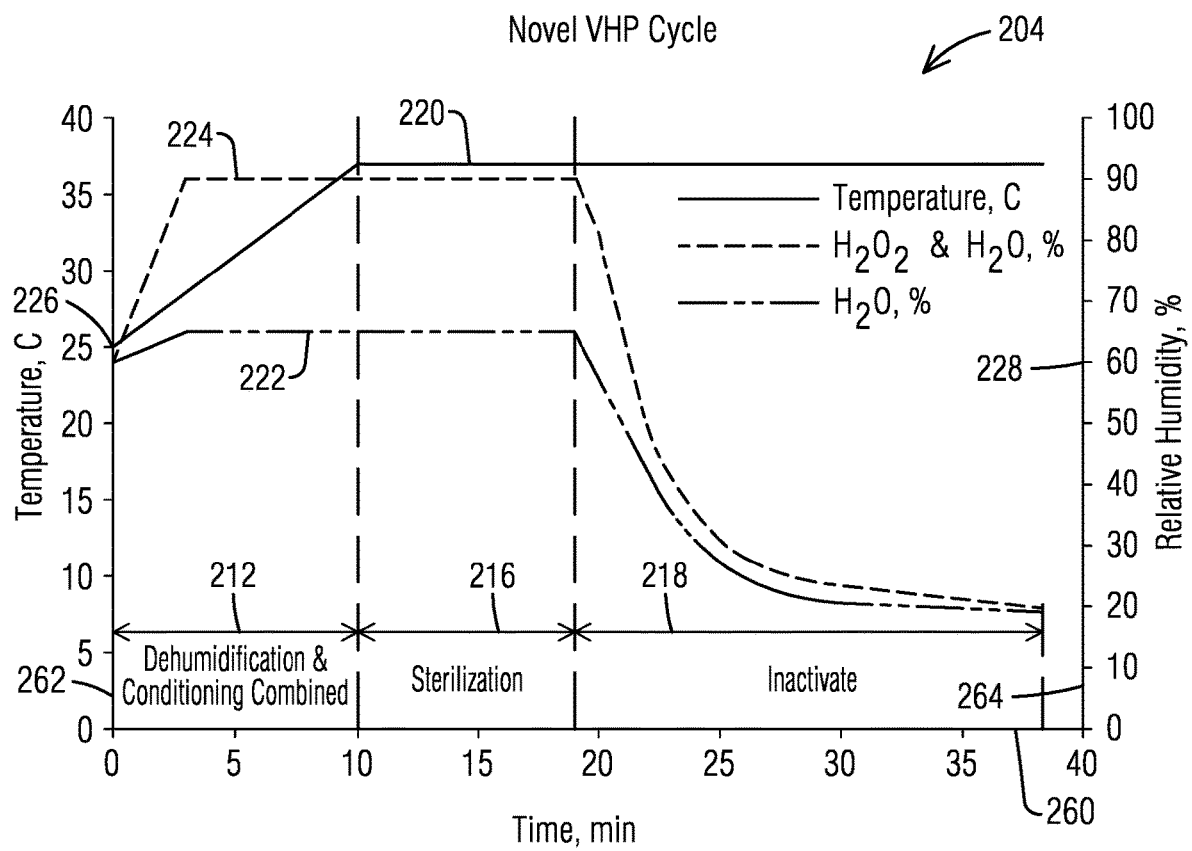
FIG. 26 is a graph that shows one embodiment of temperature and humidity levels during a H202 cleaning cycle using the system of FIG. 19.

These steps 501 and 503 of the H202 cleaning cycle are depicted in the first time period 212 of the graph 204 of FIG. 26. The temperature 220 within the interior chamber 4 is depicted as increasing from an initial temperature 226 (e.g. 25C) to the sterilizing temperature (e.g. 37C) over the first time period 212. Additionally, during the same time period 212 a combined relative humidity 224 of H20 and H202 increases from an initial humidity 228 (e.g. based on the injection of H202 from the module 200 into the chamber 4) to a sterilizing level (e.g. 90%). This is distinct from the prior art H202 cleaning cycle (FIG. 18) where two separate steps are required (e.g. the first time period 312 of 10 minutes to raise the temperature and the second time period 314 of 5 minutes to raise the humidity of H202). The H202 cleaning cycle advantageously performs both of these steps in one step that lasts time period 212 (e.g. 10 minutes) that is shorter than the combined time periods 312, 314 (e.g. 15 minutes) of the prior art H202 cycle.

In step 505, after the end of the time period 212, the sterilizing temperature 220 and sterilizing combined humidity 224 are maintained within the interior chamber 4 over a minimum time period (e.g. a second time period 216, see FIG. 26). In one embodiment, the second time period 216 is 12 minutes. In this step 505, the control interface 15 transmits a signal to the temperature control unit 17 and humidity control unit 19 such that the sterilizing temperature 220 and sterilizing combined humidity 224 are maintained for the second time period 216. Additionally, the humidity sensor 31a, the control interface 15 and piezo ultrasonic device 235 continuously communicate over the minimum time period in order to maintain the sterilizing level of the combined humidity within the chamber 4 during step 505. For example, if the combined humidity of H202 and H20 drops from the sterilizing level, the control interface 15 transmits a signal to the piezo ultrasonic device 235 to inject vaporized H202 within the chamber 4 until the control interface 15 receives a signal from the humidity sensor 31a that the combined humidity is back at the sterilizing level, at which time the control interface 15 transmits a signal to deactivate the piezo ultrasonic device 235. In some embodiments, the time period 216 of the sterilizing step (e.g. 9 minutes) is shorter than the time period 316 of the sterilizing step (e.g. 11 minutes) in the prior art cycle 300.

In step 507, after the end of the second time period 216, the H202 cleaning cycle enters an inactivate step, where the level of H202 within the interior chamber 4 is reduced to safe levels. At the beginning of a third time period 218 of the step 507 (see FIG. 26), the control interface 15 transmits a signal to the fan 246 (see FIG. 23) to draw air from the interior chamber 4 into the module 200, passing the air through the catalyst 244 to reduce a level of H202 in the air, before directing the air back into the interior chamber 4 through the vent 240. In an example embodiment, the catalyst 244 is configured to reduce the H202 content within the air to vaporized water (H20) and oxygen gas (O2). In one embodiment, the control unit 15 activates the fan 246 during step 507 for the third time period 218 (e.g. 20 minutes) until the level of H202 reaches a safe level, as discussed in greater detail below. In one embodiment, once the control unit 15 confirms that the level of H202 has lowered to a safe value, the control unit 15 transmits a signal to the door lock 252 to disengage to lock 252 so that the door 5 can be opened.

The inventive H2O2 cleaning cycle is illustrated in the graph 204 of FIG. 26. Horizontal axis 260 is time in units of minutes. Left vertical axis 262 is temperature in units of Celsius (C). Right vertical axis 264 is relative humidity in percentage (%). According to this cycle, the 'dehumidification' and 'conditioning' steps of the prior art cycle 300 (during time periods 312, 314) are combined into one time period 212 that is shorter than the combined time periods 312, 314. As this inventive process begins the interior chamber 4 is heated and the temperature 220 begins to rise during the first time period 212 from an initial temperature 226 (e.g. 25C). As the temperature 220 increases the air will have a greater moisture capacity. Then a small amount of H202 is injected into the interior chamber 4 during the first time period 212. This amount of moisture is controlled to a desired sterilizing level (e.g. 90%), as discussed in step 501 above. The temperature 220 continues to rise as the H202 is injected to the chamber 4 during the first time period 212. Again, this allows the air to handle more moisture and thus more H202 is injected. These small drying & injection steps continue until the temperature 220 has reached a sterilizing temperature (e.g. 37 C). Once the temperature 220 stops increasing, the amount of moisture the air can hold also stops increasing.

In one embodiment, a process that took fifteen minutes (that is, the first time period 312 of ten minutes for the dehumidification step and the second time period 314 of five minutes for the conditioning step) in the prior art now takes only the first time period 212 which is less (e.g. ten minutes) than the combined first and second time periods 312, 314 in the prior art. In fact, because the conditioning segment of the dehumidification plus conditioning step takes only about five minutes, the humidity 224 reaches 90% before the temperature 220 reaches 37 C. See FIG. 26. This is distinct from the prior art method, where the humidity 324 reaches 90% after the temperature 320 reaches 37 C (See FIG. 18).

According to this inventive H2O2 cycle 204, heat is used to dehumidify the chamber interior 4; mechanical refrigeration is not used. Combining the two steps would not result in a beneficial outcome if dehumidification by mechanical refrigeration was used because that dehumidification process also removes H2O2 from the air. Of course, removal of H2O2 by the mechanical dehumidification would be detrimental as during the combined dehumidification and conditioning step H2O2 is being injected into the chamber 4.

At the beginning of the H2O2 decomposing step (i.e. at the beginning of the third time period 218), the fan 246 is turned on in the chamber 4 that blows air through a silver catalyst, typically in the form of a silver mesh. The catalyst converts the H2O2 to harmless H2O and O2. This fan 246 is distinct from the fan 23.

In addition to the overall shorter H2O2 cycle due to combining the first two steps, there is also more microbial 'killing' when the sterilization cycle begins. As soon as H2O2 is injected into the chamber 4, microorganisms begin to die. In the prior art H2O2 cycle, H2O2 injection was begun after an elapsed time of ten minutes (e.g. after the first time period 312).

In the inventive H2O2 cycle, H2O2 is injected immediately (e.g. at the commencement of the first time period 212) and therefore immediately begins to have an effect. In theory, this allows for a shorter sterilization cycle (e.g. a shorter second time period 216). However, in one embodiment, the sterilization time period is not reduced, relative to the sterilization time period in the prior art cycle. In other embodiments, the second time period 216 is shorter than the third time period 316 of the prior art cycle of FIG. 18.

In one embodiment, during the time interval 218 of the inventive H2O2 cleaning cycle air is blowing through the silver mesh 244.

FIG. 27 is similar to FIG. 26 but includes additional detail including separately identifying safety factor time sub-intervals that are subsumed within the time intervals illustrated in FIG. 26. These safety factors are indicated as a single value or a range of values.

In the embodiment of FIG. 27, a safety factor of about ten minutes is applied during the dehumidification and conditioning step (e.g. first time period 212), noting a relative humidity during this step of 30-100%. The inventors recognize that starting conditions for each H2O2 cycle will vary with each use. Some users may begin with their incubator at 'off' at room temperature of 20 C. Other users may have been running the incubator and it is therefore already at an elevated temperature (i.e., above room temperature, such as 25C as shown in FIG. 3). Because the starting conditions vary, the amount of biological 'kill' during this phase will also vary. In this embodiment, the inventors have estimated and therefore included a relative humidity safety factor (SF) of between 30% SF and 100%. This SF between 30% and 100% indicates that the combined dehumidification and condition step discussed herein over the first time period 212 is sufficient to destroy between 30% and 100% of the microorganisms needed to achieve sterilization. In some embodiments, one or more biological indicators (BI's) are placed inside the chamber 4 prior to the dehumidification and condition step (i.e. prior to the first time period 212) and then the number of killed BI's is assessed after the first time period 212 (and prior to the sterilization interval 216). In some embodiments, this assessment of the BI's was performed over a variety of starting conditions, and the SF was calculated based on the resulting range of BI assessments. The embodiments of the invention are not limited to this SF and may have a wider or narrower SF, for example.

In the embodiment of FIG. 27, the sterilization interval 216 is shown as comprising two sub-intervals 216a, 216b; the first interval 216a (e.g. six minutes) and the second interval 216b (e.g. 3 minutes). The first interval 216a provides a log-6 kill, which by definition results in a sterilized environment. This metric results in the statistical destruction of all microorganisms and their spores, defined as 6 logs (10^6) or a 99.9999% reduction. Statistically an environment sterilized to this level is considered to have zero viable organisms surviving.

However, again the inventors recognize the need to compensate for chamber variations and have therefore added a safety factor to the sterilization interval. In one embodiment a 50% safety factor, equivalent to the second interval 216b (e.g. three minutes or 50% of six minutes) that is 50% as long as the first interval 216a is used.

However, the sterilization interval is not limited to the interval 216a, 216b depicted in FIG. 27. FIG. 28 depicts another embodiment of a sterilization interval 216' that provides a log-12 kill, that is based on a doubling of the log-6 kill time 216a (e.g. six minutes), resulting in 12 minutes. The 50% safety factor interval (e.g. six minutes or 50% of twelve minutes) was added to the 12 minutes, resulting in a total 18 minute time period for the sterilization interval 216'.

FIG. 27 includes a reference to a H2O2 level (e.g. 75 ppm) during the time period 218 of the inactivate cycle. The time period 218a is based on the amount of time it takes to reduce the H2O2 to this level. This H2O2 level value, which is also applied in the FIG. 26 although not labeled on FIG. 26, represents the IDLH (Immediate Dangerous to Life or Health) limit as defined by OSHA (Occupational Safety and Health Administration). In theory, when the H2O2 in the chamber 4 has been reduced to this H2O2 level the user can open the chamber door 5 as the air in the interior environment is safe. In fact the concentration would be diluted with room air, causing the level to drop by half in a few seconds. However, in one embodiment, the inventors have selected to add an additional time period 218b to the time period 218, to inactivate to at least 150% more than IDLH level before the door 5 can be opened. In other embodiments, the inventors have selected to inactivate to a level where it is safe for the operator to open the door. The safety factor has been added to ensure that the level of H2O2 has been reduced to a safe value. Again, the safety factor compensates for chamber variations and tolerances, such as instrumentation measurement accuracy.

However, the time period of the inactivate cycle is not limited to the time periods 218a, 218b depicted in FIG. 27. FIG. 28 depicts another embodiment of a time period 218' of an inactivate cycle that provides a minimum time period (e.g. 60 minutes) for the inactivate cycle that is greater than the combined time periods 218a, 218b. In some embodiments, after the time period 218' has elapsed and humidity sensors verify that the H2O2 level is below a safe level, the door can be opened.

The inventive H2O2 cycle (including the indicated safety factors) is shorter (e.g. seven minutes shorter) than the prior art cycles. In an embodiment, the first time period 212 is shorter (e.g. 5 minutes) than the combined time periods 312, 314 of the prior art cycle 300, where the first time period 212 combines the dehumidification (time period 312) and conditioning (time period 314) steps of the prior art cycle 300. In another embodiment, the sterilization time period 216 is shorter (e.g. 2 minutes) than the sterilization time period 314 of the prior art cycle 300. This shortened sterilization time period 216 is attributable to injecting H2O2 into the chamber 4 at an earlier stage (first time period 212) in the inventive H2O2 cycle than at a later stage (second time period 314) in the prior art cycle 300. Thus, a greater number of microorganisms are killed prior to the sterilization time period 216 in the inventive cycle than the sterilization time period 316 in the prior art cycle 300. Accordingly, the sterilization time period 216 need not be as long in the inventive H2O2 cycle as the sterilization time period 316 in the prior art cycle 300. This reduced cleaning cycle time is advantageous for the chamber user as the reduction in cleaning time allows for additional time to be devoted to culturing cells within the chamber 4.

Certain other features of incubation chambers are described in commonly-owned patent applications that are incorporated herein by reference: application entitled Insulated Chamber with Phase Change Material and Door with Controlled Transparency, filed on Jul. 23, 2015 and assigned application No. 62/195,960; and application entitled Insulated Chamber with Phase Change Material, filed on Mar. 9, 2015 and assigned application Ser. No. 14/641,607.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A system for vaporized hydrogen peroxide cleaning of a chamber of a container, said system comprising:
   a temperature altering device configured to alter a temperature of air in the chamber from an initial temperature to a sterilization temperature over a first time period; and
   an injection item configured to inject vaporized hydrogen peroxide into air in the chamber during the first time period to alter a relative humidity of hydrogen peroxide vapor in the chamber to a sterilization level over the first time period.

2. The system according to claim 1 wherein the temperature altering device and the injection item are configured to be selectively activated during a second time period after the first time period to maintain the temperature at the sterilization temperature and the relative humidity at the sterilization level over the second time period.

3. The system according to claim 2, further comprising a catalyst configured to reduce the relative humidity from the sterilization level to a safe level over a third time period after the second time period based on air being passed through the catalyst.

4. The system according to claim 3, further comprising a fan configured to direct air from within the chamber through the catalyst.

5. The system according to claim 4, wherein the catalyst is positioned within the chamber and wherein the fan is configured to direct air from the chamber through the catalyst during the third time period such that the catalyst converts the hydrogen peroxide vapor to water and oxygen gas.

6. The system according to claim 5, wherein the injection item is a removable module positioned within the chamber and wherein the fan and the catalyst are positioned within the removable module such that the fan is configured to draw air from the chamber into the module such that the air passes through the catalyst and is exhausted through a vent of the module and into the chamber.

7. The system according to claim 6, further comprising:
   the catalyst positioned between the vent and the fan;
   wherein the vent is defined by a removable piece disposed at an end of the module, wherein the removable piece is configured to be removed from the module to expose the catalyst.

8. The system according to claim 7, further comprising:
   a pair of wires coupled to respective connections of the catalyst;
   wherein the wires and respective connections are configured such that a signal can be applied to the wires across the respective connections to measure one or more electrical properties of the catalyst.

9. The system according to claim 1, wherein the injection item is configured such that the relative humidity reaches the sterilization level before the temperature reaches the sterilization temperature within the first time period.

10. The system according to claim 1, wherein the injection item is configured to be positioned within the chamber.

11. The system according to claim 10, wherein the injection item comprises a removable module configured to be positioned within the chamber.

12. The system according to claim 11, wherein the injection item comprises a plurality of removable modules positioned within the chamber.

13. The system according to claim 11, wherein the removable module comprises:
   a receptacle configured to be opened; and
   a disposable H2O2 cartridge configured to be inserted into the receptacle.

14. The system according to claim 13, wherein the removable module comprises a handle and wherein at least one of:
   the receptacle is configured to be opened based on the handle being moved from a first position to a second position; and
   the module is configured to be positioned within the chamber based on holding the handle to move the module into the chamber.

15. The system according to claim 11, wherein the injection item is a piezo ultrasonic device of the module;
   and wherein the system further comprises a control interface configured to transmit a signal to the piezo ultrasonic device of the module to inject vaporized hydrogen peroxide from within the interior chamber into air in the interior chamber.

16. The system according to claim 1, further comprising:
   a temperature sensor configured to be positioned within the chamber to measure the temperature of air in the interior chamber; and
   a processor configured to receive data indicating the measured temperature from the temperature sensor and further configured to compare the measured temperature and the sterilization temperature;
   wherein the processor is configured to transmit a signal to the temperature altering device to activate the temperature altering device to alter the temperature within the interior chamber based on the comparison of the measured temperature and the sterilization temperature.

17. The system according to claim 1, further comprising:
   a humidity sensor configured to be positioned within the interior chamber to measure the relative humidity of hydrogen peroxide in the interior chamber; and
   a processor configured to receive data from the humidity sensor indicated the measured relative humidity and to compare the measured relative humidity and the sterilization level;
   wherein the processor is configured to transmit a signal to the injection item to activate the injection item to inject vaporized hydrogen peroxide from within the interior chamber into air in the interior chamber to increase the relative humidity of hydrogen peroxide vapor in the interior chamber based on the comparison of the measured relative humidity and the sterilization level.

18. A system for vaporized hydrogen peroxide cleaning of a chamber of a container, said system comprising:
- a temperature sensor configured to measure a temperature of air in the chamber;
- a humidity sensor configured to measure a relative humidity of hydrogen peroxide in the chamber;
- a processor communicatively coupled to the temperature sensor and the humidity sensor to receive data indicating the measured temperature and the measured relative humidity from the temperature sensor and the humidity sensor;
- a temperature altering device configured to alter a temperature of air in the chamber; and
- an injection item configured to inject vaporized hydrogen peroxide into air in the chamber;
- wherein the processor is configured to compare the measured temperature with a sterilization temperature and further configured to transmit a first signal to the temperature altering device over a first time period such that the temperature altering device increases the temperature of air in the chamber from an initial temperature to the sterilization temperature over the first time period; and
- wherein the processor is configured to compare the measured humidity with a sterilization level and further configured to transmit a second signal to the injection item over the first time period such that the injection item injects vaporized hydrogen peroxide into air in the chamber to increase the relative humidity of hydrogen peroxide in the chamber from an initial level to the sterilization level over the first time period.

19. The system according to claim 18,
- wherein the processor is configured to transmit a third signal to the temperature altering device and a fourth signal to the injection item during a second time period after the first time period to maintain the temperature at the sterilization temperature and the relative humidity at the sterilization level over the second time period; and
- wherein the system further comprises a catalyst configured to reduce the relative humidity from the sterilization level to a safe level over a third time period after the second time period based on air being passed through the catalyst.

20. An improvement for a system for vaporized hydrogen peroxide cleaning of a container comprising a temperature altering device configured to alter a temperature of air in the chamber from an initial temperature to a sterilization temperature over a first time period and an injection item configured to inject vaporized hydrogen peroxide into air in the chamber over a second time period after the first time period to alter a relative humidity of hydrogen peroxide vapor in the chamber to a sterilization level over the second time period, wherein the improvement comprises:
- the temperature altering device being configured to alter the temperature of air in the chamber to the sterilization temperature and the injection item being configured to alter the relative humidity of hydrogen peroxide vapor to the sterilization level over the same first time period.

* * * * *